(12) United States Patent
Ravi

(10) Patent No.: US 7,670,794 B2
(45) Date of Patent: Mar. 2, 2010

(54) MANAGING GLYCEMIA STATUS IN DIABETIC PATIENTS

(75) Inventor: Nathan Ravi, Chesterfield, MO (US)

(73) Assignee: Washington University, St. Louis, MO (US)

( * ) Notice: Subject to any disclaimer, the term of this patent is extended or adjusted under 35 U.S.C. 154(b) by 182 days.

(21) Appl. No.: 11/555,330

(22) Filed: Nov. 1, 2006

(65) Prior Publication Data
US 2007/0111272 A1 May 17, 2007

Related U.S. Application Data

(60) Provisional application No. 60/733,821, filed on Nov. 4, 2005.

(51) Int. Cl.
*C12Q 1/54* (2006.01)
(52) U.S. Cl. ....................................... 435/14
(58) Field of Classification Search .................... 435/14
See application file for complete search history.

(56) References Cited

U.S. PATENT DOCUMENTS

| 2002/0055458 | A1 | 5/2002 | Stefansson | |
|---|---|---|---|---|
| 2003/0187074 | A1 | 10/2003 | Hussain et al. | |
| 2007/0110707 | A1* | 5/2007 | Ravi | 424/78.12 |

OTHER PUBLICATIONS

Kunica K. et al. Physiologic Concentrations of Inorganic Phosphate Accelerate Fructosamine Synthesis. Diabetes Research and Clinical Practice. 17(1)Jul. 9-16, 1992.*
Okazaki R. et al. Metabolic Improvement of Poorly Controlled Noninsulin Dependent Diabetes Mellitus Decreases Bone Turnover. J of Clinical Endocrinology and Metabolism. 82(9)2915-2920, 1997.*
Ratkovic-Gusic et al, Disturbances of phosphate balance: hypophsophatemia, Acta Clin Croat, 2004, 43:67-73.
Hudson et al, Glycation and Diabetes: The RAGE connection, Current Science, 2002, 83:1515-1521.
Dobnig et al, Type 2 diabetes mellitus in nursing home patients: effects on bone turnover, bone mass, and fracture risk, J Clin Endocrinol Metab, 2006, 91:3355-3363.
Brownlee, Lilly Lecture 1993. Glycation and diabetic complications. Diabetes 1994,43:836.
Haley and Ward, Nonenzymatically glucosylated serum proteins in patients with end-stage renal disease. Am. J. Kidney Dis. 1986, 8:115-121.
Hunt and Wolff, The role of histidine residues in the nonenzymic covalent attachment of glucose and ascorbic acid to protein. Free Radical Research Communications 1991,12-13 Pt 1:115.
Kimura et al, Identification of advanced glycation end products of the Maillard reaction in Pick's disease. Neuroscience Letters 1996, 219:95.
Kunika et al, Correction of fructosamine value for serum albumin and globulin concentrations. Diabetes Research and Clinical Practice 1991, 13:37.
Kunika et al, Inorganic phosphate accelerates hemoglobin A1c synthesis. Life Sciences 1989, 45:623.
Kunika et al, Physiologic concentrations of inorganic phosphate accelerate fructosamine synthesis. Diabetes Research and Clinical Practice 1992, 17:9.
Monnier et al, Structure of advanced Mai!lard reaction products and their pathological role Nephrology, Dialysis, Transplantation 1996, 11 Suppl 5:20.
Monnier et al, the Mechanism of Collagen Cross-Linking in Diabetes A Puzzle Nearing Resolution Diabetes 1996, 45 Suppl 3:S67.
Odetti et al, Chromatographic quantitation of plasma and erythrocyte pentosidine in diabetic and uremic subjects. Diabetes 1992, 41:153.
Pongor et al, Aging of proteins: isolation and identification of a fluorescent chromophore from the reaction of polypeptides with glucose. PNAS 1984, 81:2684.
Sabater et al, Nonenzymatic glycosylation of hemoglobin and total plasmatic proteins in end-stage renal disease. Am. J. Nephrol. 1991,11:37-43.
Wolff and Dean, Glucose autoxidation and protein modification. The potential role of 'autoxidative glycosylation' in diabetes. Biochemical Journal 1987, 245:243.

* cited by examiner

*Primary Examiner*—Ralph Gitomer
(74) *Attorney, Agent, or Firm*—Sonnenschein, Nath & Rosenthal LLP

(57) ABSTRACT

Methods for monitoring and managing glycemia status in a diabetic patient are disclosed. The methods comprise measuring in a diabetic patient, serum concentrations of HbA1c, glucose and inorganic phosphate and comparing the measured concentrations with reference concentrations. An equation representing the reference relationship of HbA1c, glucose and inorganic phosphate is also provided.

17 Claims, 11 Drawing Sheets

MANAGING GLYCEMIA STATUS IN DIABETIC PATIENTS

RELATED APPLICATION

This application claims the priority of provisional application No. 60/733,821 filed Nov. 4, 2005, which is fully incorporated by reference as if fully set forth herein.

FIELD

This invention relates generally to diabetes and, more particularly, to methods for monitoring and managing glycemia status in diabetic patients based upon HbA1c, glucose and phosphate levels.

BACKGROUND

Diabetic complications are believed to involve elevated amounts of advanced glycation end products (AGE's) (Vlassara et al., *Lab. Invest.* 70:138-151, 1994; Jakus et al., *Physiol. Res.* 53:131-142, 2004). AGE's are formed by the non-enzymatic reaction of amino acids and amino groups of proteins with reducing sugars (Maillard, *CR Acad. Sci.* 154:66-8, 1912). The AGE's thus formed can eventually cross link with peptides and proteins to form complexes that can lead to diabetic complications (for review see Bucala et al., *Adv. Pharmacol.* 23:1-34, 1992; Brownlee, *Metabolism* 49:9-13, 2000; Singh et al., *Diabetologia* 44:129-146, 2001).

One detectable measure of glycation is the formation of fructose amine on plasma proteins like human serum albumin as well as serum HbA1c, both by the non-enzymatic glycation reaction of hemoglobin with glucose (McDonald et al., *J. Biol. Chem.* 253:2327-2332, 1978). Both fructose amine and the HbA1c levels in diabetic patients have been shown to reflect mean blood glucose concentration over the previous two weeks to almost four months, thus providing a way of documenting the degree of control of glucose metabolism (Koenig et al., *N. Engl. J. Med.* 295:417-420, 1976). Of the two indicators, the relationship between HbA1c and plasma glucose has been defined based upon a regression analysis of values observed in a multicenter clinical trial and the relationship has been reported to be useful in diabetes control (Rohlfing et al., *Diabetes Care* 25:275-8, 2002).

Factors other than glucose have also been reported to influence non-enzymatic glycation including oxygen tension and 2,3-diphosphoglycerate concentrations which is an example of an organic phosphate catalyzed glycation (Smith et al., *J. Clin. Invest.* 69:1164-1168, 1982). Increasing phosphate concentrations have also been reported to enhance glycation in vitro (Hall et al. *Biochimica et Biophysica Acta* 993:217-223, 1989; Kunika et al., *Life Sci.* 45:623-630, 1989; Kunika et al., *Diabetes Research and Clinical Practice* 17:9-16, 1992). In addition, in non-diabetic healthy humans, inorganic phosphate concentrations have been reported to be significantly correlated to the levels of the glycation product, fructosamine, corrected for glucose concentrations. (Kunika, supra, 1992). The magnitude of protein glycation was estimated in this report from blood glucose concentration and inorganic phosphorus concentration based upon an in vitro rate of glycation (Id.). Nevertheless, the combined role of HbA1c, glucose and inorganic phosphorus concentrations in determining glycemia status in diabetic patients has not been heretofore defined.

SUMMARY

Accordingly, the present inventor has succeeded in discovering that HbA1c, glucose and inorganic phosphorus levels are interrelated and can be incorporated into a method of monitoring and controlling glycemia levels in diabetic patients. The interrelationship of HbA1c, glucose and inorganic phosphorus levels forms the basis for using all three parameters to monitor the glycemia status of diabetic patients and provides a rationale for treating the patients with interventions that alter glucose levels, inorganic phosphate levels or both. Phosphorus serum levels are predominantly inorganic phosphate levels, however, organic phosphates or the total of inorganic and organic phosphate levels can also show a relationship with glycation products and glucose. Thus, the use of total or organic phosphate serum levels in the above relationship for monitoring and treating diabetic patients is also within the scope of the present invention.

Thus, in various embodiments, the present invention is directed to a method of managing glycemia in a diabetic patient. The method can comprise (a) measuring in a diabetic patient, serum concentrations of HbA1c, glucose and inorganic phosphate and (b) comparing measured concentrations of HbA1c, glucose, and inorganic phosphate with reference concentrations of HbA1c, glucose, and inorganic phosphate, wherein if any one or more of measured concentrations of HbA1c, glucose, and inorganic phosphate exceed reference concentrations, glycemia is deemed to not be controlled. In various embodiments, the reference concentrations for serum glucose, serum inorganic phosphate and serum HbA1c can be about 140 mg/dL, about 4.5 mg/dL and about 7%, respectively. In various embodiments, the comparing can comprise determining that (i) if the measured serum glucose concentration exceeds about 140 mg/dL, serum glucose concentration is deemed to not be controlled; (ii) if the measured serum inorganic phosphate concentration exceeds 4.5 mg/dL, serum inorganic phosphate concentration is deemed to not be controlled; and (iii) if the measured serum HbA1c concentration exceeds 7% (w/v), both serum glucose concentration and serum inorganic phosphate concentrations are deemed to not be controlled.

In various embodiments, the method can further comprise managing glycemia level in the patient. Such managing can comprise administering one or more agents that decrease serum glucose concentration, administering one or more agents that decrease serum inorganic phosphate concentration or administering one or more agents that decrease serum glucose concentration and one or more agents that decrease serum inorganic phosphate concentration. In various embodiments, the managing can be such that (i) if measured serum glucose concentration exceeds about 140 mg/dL, glycemia is deemed to not be controlled and managing comprises administering one or more agents that decrease glucose concentration; (ii) if measured serum inorganic phosphate concentration exceeds about 4.5 mg/dL, inorganic phosphate concentration is deemed to not be controlled and managing comprises administering one or more agents that decrease inorganic phosphate concentration; and (iii) if measured serum HbA1c concentration exceeds 7% (w/v), both glucose concentration and inorganic phosphate concentration are deemed to not be controlled and managing comprises administering one or more agents that decrease glucose concentration and one or more agents that decrease inorganic phosphate concentration.

In various embodiments, the present invention can involve additional approaches for monitoring and managing glycemia status in a diabetic patient. Such approaches can involve methods comprising measuring in a diabetic patient, serum concentrations of HbA1c, inorganic and organic phosphate and glucose and calculating an estimated value for glucose concentration based upon a reference relationship of HbA1c, inorganic or total phosphate and glucose levels. The reference relationship can be represented in the equation:

$$G_e = A \times Hb - B \times P_i - C$$

wherein $G_e$ is estimated serum glucose concentration, Hb is measured serum HbA1c concentration, $P_i$ is measured serum inorganic phosphate concentration or total phosphate concentration, A is about 76, B is about 67 and C is about 212. The method can further involve comparing measured serum glucose concentration and estimated serum glucose concentration to a reference glucose concentration. The reference serum glucose concentration can be about 140 mg/dL. The comparing can involve a determination such that if either or both of the measured serum glucose concentration and the estimated serum glucose concentration exceed the reference glucose concentration, glycemia is deemed to not be controlled.

In various aspects, the method can further comprise managing glycemia level in the patient. Such managing of the glycemia levels can comprise administering one or more agents that decrease serum glucose concentration, administering one or more agents that decrease serum inorganic phosphate concentration or administering one or more agents that decrease serum glucose concentration and one or more agents that decrease serum inorganic phosphate concentration. In various embodiments, the managing can be such that (i) if measured serum glucose concentration exceeds about 140 mg/dL and estimated serum glucose concentration does not, glycemia is deemed to not be controlled and managing comprises administering one or more agents that decrease serum glucose concentration; (ii) if estimated serum glucose concentration exceeds about 140 mg/dL and measured serum glucose concentration does not, inorganic phosphate concentration is deemed to not controlled and managing comprises administering one or more agents that decrease serum inorganic phosphate concentration and (iii) if both measured serum glucose concentration and estimated serum glucose concentration exceed about 140 mg/dL, glycemia and inorganic phosphate concentrations are deemed to not be controlled and managing comprises administering one or more agents that decrease serum glucose concentration and one or more agents that decrease serum inorganic phosphate concentration.

In various embodiments, the one or more agents that decreases serum inorganic phosphate concentration can be a diuretic having carbonic anhydrase activity, a phosphate binder or a combination thereof. The diuretic can be acetazolamide, dichlorphenamide, methazolamide, furosemide or a combination thereof. The phosphate binder can be aluminum hydroxide; calcium hydroxide; a calcium salt such as calcium acetate, calcium carbonate, calcium gluconate or a combination thereof; magnesium hydroxide; a magnesium salt such as magnesium acetate, magnesium carbonate, magnesium gluconate or a combination thereof; lanthanum carbonate, a phosphate binding cationic polymer or a combination thereof. In particular, the phosphate binder can be lanthanum carbonate or the phosphate binding cationic polymer, sevelamer hydrochloride.

In various embodiments, the one or more agents that decrease serum glucose concentration can be insulin, a sulfonylurea, a biguanide compound, a meglitinide compound, a compound that acts upon starch digestion or metabolism or a combination thereof.

In various embodiments, the present invention can also comprise assay kits for determining glycemia status in a patient, the kits comprising reagents for measuring glucose levels, HbA1c levels, and inorganic phosphate levels in a sample obtained from the patient. Such kits can be used in diagnosis of a diabetic condition in a patient as well as in monitoring the glycemia status of a diabetic patient.

DETAILED DESCRIPTION

Figure 1A:
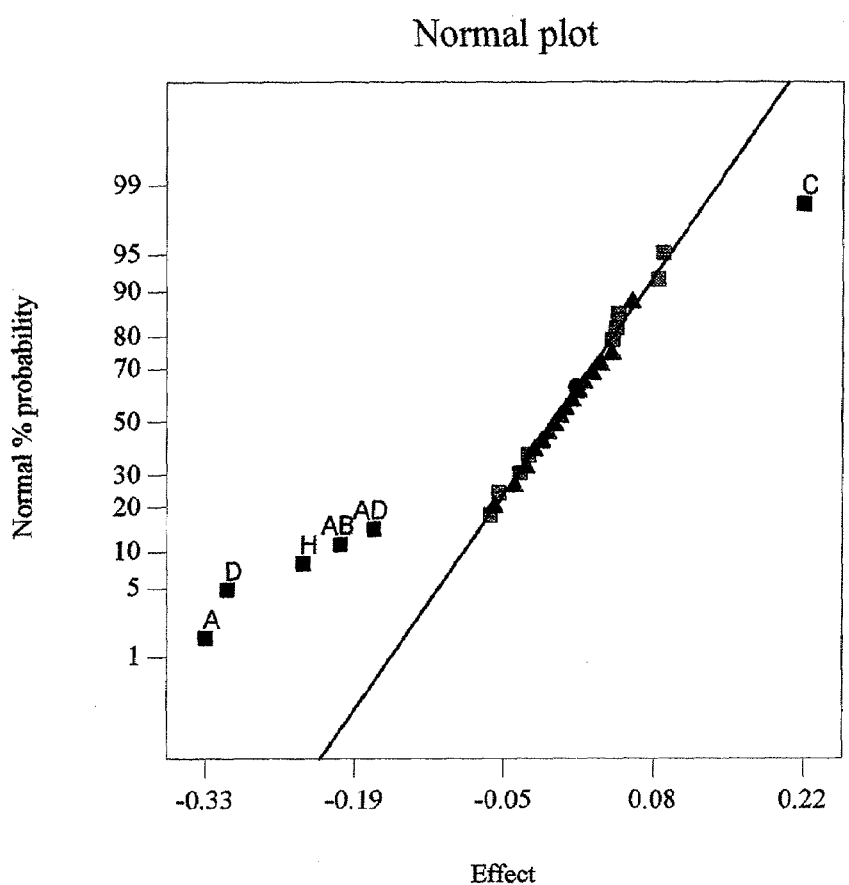
FIG. 1 illustrates (A) the normal % probability plot of factors that influence pH, (B) the expected random distribution of Studentized residuals on a normal plot and (C) the interactions of oxygen with phosphate and ribose shown as a cubic plot.

The present invention can involve a method of monitoring and controlling glycemia levels in diabetic patients based upon the relationship of HbA1c, glucose and inorganic phosphorus levels which takes into account all three values in monitoring the glycemia status of the patient and provides a basis for treating the patient with interventions that alter glucose levels, inorganic phosphate levels or both.

Patients having diabetes can be identified based upon diagnostic criteria established by the National Diabetes Data Group of the National Institutes of Health (Report of the Expert Committee on the Diagnosis and Classification of Diabetes Mellitus. *Diabetes Care* 20:1183-97, 1997). Accordingly, diabetes mellitus can be diagnosed on the basis of positive findings from any two of the following tests on different days: (1) Symptoms of diabetes mellitus (polyuria, polydipsia or unexplained weight loss) plus casual (i.e. any time of day without regard to time since last meal) plasma glucose concentration equal to or greater than 200 mg/dL (11.1 mmol/L) or (2) Fasting plasma glucose equal to or greater than 126 mg/dL (7.0 mmol/L) or (3) two-hour postprandial glucose following ingestion of 75 g of glucose is equal to or greater than 200 mg/dL (11.1 mmol/L) (Id.).

HbA1c is a stable minor component making up from 3-6% of total hemoglobin (Koenig et al., *J. Biol. Chem.* 252:2992-7, 1977). This hemoglobin variant has been shown to be formed by the direct reaction of hemoglobin with glucose (McDonald et al., *J. Biol. Chem.* 253:2327-2332, 1978).

HbA1c levels have been reported to reflect the mean blood sugar concentration over previous weeks to months (Koenig et al., *N. Eng. J. Med.* 295:417-20, 1976). Thus, monitoring HbA1c levels may be particularly useful in monitoring glycemia control in diabetes (Cerami et al., *Metabolism* 28(*Suppl*):431-437, 1979).

Reference herein to serum levels of HbA1c or to serum concentrations of HbA1c are intended to be interchangeable and such references are intended to include levels or concentrations of HbA1c measured in serum, plasma, whole blood or any fraction thereof as well as any indirect estimation of serum inorganic phosphate levels from levels or concentrations in any other sample obtained from the patient. HbA1c levels can be measured by methods known in the art (see for example, John, Haemoglobin A1c: analysis and standardisation, *Clin. Chem. Lab. Med.* 41(9):1199-212, 2003; Lee et al., Glycohaemoglobin measurement: methodological differences in relation to interference by urea, *Acta Diabetol.* 39(1): 35-9, 2002; Matteucci et al., Glycated hemoglobin measurement: intermethod comparison, *Diabetes Nutr. Metab.* 14(4): 217-9, 2001). Such methods include HPLC methods and immunoturbidimetric assays. Enzymatic assay can also be used based upon fructosyl amino acid oxidase enzymes (see for example, U.S. Pat. Nos. 6,127,138; 6,033,867; 5,972,671, 5,948,659, which are incorporated by reference) or fructosyl valine oxidase assay (Glycated Hemablobin HbA1c Kit, Diazyme Laboratories, San Diego, Calif.). Typically, HbA1c levels are measured in samples of whole blood that has been lysed and treated with a protease enzyme. Normal values of HbA1c in adult humans can range from about 4.0 to about 6.0 and the target level for diabetic patients can be less than about 7%.

Reference herein to serum levels of glucose or to serum concentrations of glucose are intended to be interchangeable and such references are intended to include levels or concentrations of glucose measured in serum, plasma, whole blood or any fraction thereof as well as any indirect estimation of serum inorganic glucose levels from levels or concentrations in any other sample obtained from the patient. Glucose levels are usually measured by enzymatic assay with photometric detection. Typical enzymatic serum glucose assays can be base upon glucose oxidase or hexokinase (see for example, Giampietro et al., *Clin. Chem.* 28:2405-7, 1982, which are incorporated by reference). Normal levels for serum glucose can be less than about 110 mg/dL.

Reference herein to serum levels of inorganic phosphate or to serum concentrations of inorganic phosphate are intended to be interchangeable and such references are intended to include levels or concentrations of inorganic phosphate measured in serum, plasma, whole blood or any fraction thereof as well as any indirect estimation of serum inorganic phosphate levels from levels or concentrations in any other sample obtained from the patient. Serum inorganic phosphate levels are usually measured spectrophotometrically as the complex of phosphate ions with ammonium molybdate and levels are usually expressed in terms of phosphorus content (see, for example Cogan et al., *Anal Biochem.* 271:29-35, 1999 which is incorporated by reference). Normal levels of serum inorganic phosphate in humans range from about 2.5 to about 4.5 mg/dL in adults and from about 3 to about 6 mg/dL in children.

In various embodiments, the glycemia status of a diabetic patient can be determined from values of serum glucose, HbA1c and inorganic phosphate concentrations in the patient. Assay systems for measuring serum glucose, HbA1c and inorganic phosphate levels can be adapted for use in assay kits. Thus, in various embodiments, the present invention can comprise assay kits for monitoring glycemia status in a diabetic patient, the kits comprising reagents for measuring serum glucose, HbA1c and serum inorganic phosphate in a sample obtained from the patient. Reagents for measuring serum glucose levels can include glucose oxidase or hexokinase; reagents for measuring serum HbA1c can comprise fructosyl amino acid oxidase, and in particular, fructosyl valine oxidase; and reagents for measuring serum inorganic phosphate levels in a sample can comprise ammonium molybdate. These and other methods can be adapted for application in the assay kits for determining serum glucose levels, HbA1c levels and serum inorganic phosphate levels.

Various different approaches can then be used in assessing the values thus obtained. The measured values can then be compared with reference values for serum glucose, inorganic phosphate and HbA1c concentrations. One approach for this comparison is to directly compare measured values with reference values and typical reference concentrations that can be used for serum glucose, serum inorganic phosphate and serum HbA1c can be about 140 mg/dL, about 4.5 mg/dL and about 7%, respectively. In general, reference values that can also be used in the methods of the present invention include glucose levels of about 120, about 130, about 140 or about 150, inorganic phosphate levels of about 4.0, about 4.5, about 5.0, about 5.5 or about 6.0 and HbA1c levels of about 6%, about 6.5%, about 7%, and about 7.5%.

In such instances in which the reference values for serum glucose, serum inorganic phosphate and serum HbA1c are about 140 mg/dL, about 4.5 mg/dL and about 7%, respectively, the comparison to reference values can be such that (i) if the measured serum glucose concentration exceeds about 140 mg/dL, serum glucose concentration is deemed to not be controlled; (ii) if the measured serum inorganic phosphate concentration exceeds 4.5 mg/dL, serum inorganic phosphate concentration is deemed to not be controlled; and (iii) if the measured serum HbA1c concentration exceeds 7% (w/v), both serum glucose concentration and serum inorganic phosphate concentrations are deemed to not be controlled.

Another approach for comparing measured values for serum glucose, inorganic phosphate and HbA1c levels with reference values for serum glucose, inorganic phosphate and HbA1c levels can involve the use of a reference relationship for glucose, inorganic phosphate and HbA1c. Such a reference relationship can be obtained, for example, from a reference group of patients or from a clinical trial. One such relationship obtained as discussed below in Example 2 is as follows.

$$G = A \times Hb - B \times P_i - C$$

in which G is serum glucose concentration, Hb is measured serum HbA1c concentration, $P_i$ is measured serum inorganic phosphate concentration, A is about 76, B is about 67 and C is about 212. This equation can be used to obtain an estimated value for any one of the parameters in the equation and such an estimation value for glucose levels based upon phosphate and HbA1c levels is as follows.

$$G_e = A \times Hb - B \times P_i - C$$

in which $G_e$ is estimated serum glucose concentration and Hb, $P_i$, A, B and C are as defined above. This estimated value for glucose can then be compared with the measured values of glucose and both can be compared to reference values for glucose. This comparison of estimated glucose levels is believed to represent an average glucose concentration over the previous several weeks in the patient. It represents a more accurate estimation than the concentration of HbA1c alone because it also incorporates inorganic phosphate concentration. The comparison of estimated glucose, measured glucose and reference glucose values provides a new approach for monitoring glycemia status in the diabetic patient.

Managing glycemia status in a diabetic patient can then be accomplished by deciding whether a treatment or modification of a treatment is appropriate for the patient. Such treatment or modification of treatment can involve administering one or more agents that decrease serum glucose concentration, administering one or more agents that decrease serum inorganic phosphate concentration or administering one or more agents that decrease serum glucose concentration and one or more agents that decrease serum inorganic phosphate concentration.

In approaches in which measured values of glucose, inorganic phosphate and HbA1c are compared to reference values, managing glycemia status can be such that (i) if measured serum glucose concentration exceeds about 140 mg/dL, glycemia is deemed to not be controlled and one or more agents that decrease glucose concentration can be administered to the patient; (ii) if measured serum inorganic phosphate concentration exceeds about 4.5 mg/dL, inorganic phosphate concentration is deemed to not be controlled and one or more agents that decrease inorganic phosphate concentration can be administered to the patient; and (iii) if measured serum HbA1c concentration exceeds 7% (w/v), both glucose concentration and inorganic phosphate concentration are deemed to not be controlled and both one or more agents that decrease glucose concentration and one or more agents that decrease inorganic phosphate concentration can be administered to the patient.

In approaches in which the measured values for glucose, inorganic phosphate and HbA1c are compared to a reference relationship for glucose, inorganic phosphate and HbA1c, and an estimated glucose value is calculated as described above, managing glycemia status can be such that (i) if measured serum glucose concentration exceeds about 140 mg/dL and estimated serum glucose concentration does not, glycemia is deemed to not be controlled and one or more agents that decrease serum glucose concentration can be administered to the patient; (ii) if estimated serum glucose concentration exceeds about 140 mg/dL and measured serum glucose concentration does not, inorganic phosphate concentration is deemed to not controlled and one or more agents that decrease serum inorganic phosphate concentration can be administered to the patient and (iii) if both measured serum glucose concentration and estimated serum glucose concentration exceed about 140 mg/dL, glycemia and inorganic phosphate concentrations are deemed to not be controlled and one or more agents that decrease serum glucose concentration and one or more agents that decrease serum inorganic phosphate concentration can be administered to the patient.

Serum inorganic phosphate levels can be decreased by different approaches known in the art. For example, diuretics such as, for example carbonic anhydrase inhibitors can increase renal excretion of inorganic phosphate and thereby decrease serum phosphate levels. Such carbonic anhydrase inhibitor diuretic agents include acetazolamide, dichlorphenamide, methazolamide. In addition, other classes of diuretic agents can also exhibit carbonic anhydrase activity and, as a result, increase renal excretion of inorganic phosphate. Such agents include some of the sulfonamide-based loop diuretics such as, for example, furosemide.

Inorganic phosphate levels in the serum can also be decreased by oral administration of phosphate binding agents. Phosphate binding agents combine with phosphate in the gastrointestinal tract to form a complex that is not absorbed into the blood stream. Phosphate binding agents can include, for example, aluminum hydroxide, calcium salts, such as calcium acetate, calcium carbonate or calcium gluconate, magnesium compounds such as magnesium hydroxide, magnesium acetate, magnesium carbonate or magnesium gluconate, lanthanum carbonate or phosphate binding cationic polymers such as sevelamer hydrochloride or combinations thereof. Phosphate binding cationic polymers are described in U.S. Pat. No. 5,496,545 which is incorporated by reference.

In various embodiments, glycemia management in diabetic patients can involve administration of an effective amount of an agent that decreases serum inorganic phosphorus levels. As used herein, the term treatment is intended to include preventing the appearance of a disease or condition, diminishing the severity of a disease or condition or alleviating or diminishing certain aspects or symptoms of a disease or condition.

Agents that decrease serum glucose concentrations can also be administered in managing glycation. For example, in diabetic patients, insulin can be administered parenterally or a hypoglycemic agent can be administered orally to achieve glycemia control. Oral hypoglycemic agents include sulfonylureas such as acetohexamide, chlorpropanamide, tolazamide, tolbutamide, glyburide, glipizide, and glibomuride; biguanides such as metformin and buformin; or meglitinide compounds such as repaglinide and nateglinide. In such patients, additional administration of at least one agent that decreases serum inorganic phosphate concentration advantageously minimize the generation of non-enzymatic glycation products. Such combination treatment is believed to diminish the severity of conditions arising from increased glycation, thereby, slowing the progression of diabetic complications. Other hypoglycemic agents that act on carbohydrate metabolism or on carbohydrate metabolism can also be administered (see for example, U.S. Pat. No. 6,809,115; U.S. Pat. No. 6,821,977; Murai et al., *Life Sci.* 71:1405-15, 2002).

The methods of the present invention are useful in managing glycemia in mammals having diabetes. Such mammals include humans as well as non-human mammals. Non-human mammals include, for example, companion animals such as dogs and cats, agricultural animals such live stock including cows, horses and the like, and exotic animals, such as zoo animals.

In managing glycemia in accordance with the present invention, can involve either or both of administration of an agent that decreases serum inorganic phosphate concentration and administration of an agent that decreases serum glucose concentration can be performed. In such embodiments in which both are administered, such can be at the same time or at different times and by the same or different routes of administration, depending upon the particular agents used.

Administration of a diuretic compound that increases phosphate excretion or administration of a compound that decreases serum glucose concentration, other than insulin, can be by any suitable route of administration known in the art including buccal, dental, endocervical, intramuscular, inhalation, intracranial, intralymphatic, intramuscular, intraocular, intraperitoneal, intrapleural, intrathecal, intratracheal, intrauterine, intravascular, intravenous, intravesical, intranasal, ophthalmic, oral, otic, biliary perfusion, cardiac perfusion, priodontal, rectal, spinal, subcutaneous, sublingual, topical, intravaginal, transdermal, ureteral, or urethral. Dosage forms can be aerosol including metered aerosol, chewable bar, capsule, capsule containing coated pellets, capsule containing delayed release pellets, capsule containing extended release pellets, concentrate, cream, augmented cream, suppository cream, disc, dressing, elixir, emulsion, enema, extended release fiber, extended release film, gas, gel, metered gel, granule, delayed release granule, effervescent granule, chewing gum, implant, inhalant, injectable, injectable lipid complex, injectable liposomes, insert, extended release insert, intrauterine device, jelly, liquid, extended release liquid, lotion, augmented lotion, shampoo lotion, oil, ointment, augmented ointment, paste, pastille, pellet, powder, extended release powder, metered powder, ring, shampoo, soap solution, solution for slush, solution/drops, concentrate solution, gel forming solution/drops, sponge, spray, metered spray, suppository, suspension, suspension/drops, extended release suspension, swab, syrup, tablet, chewable tablet, tablet containing coated particles, delayed release tablet, dispersible tablet, effervescent tablet, extended release tablet, orally disintegrating tablet, tampon, tape or troche/lozenge.

In embodiments in which insulin is administered to decrease serum glucose concentrations, administered is usually by a parenteral route.

In some instances, the oral route of administration can particularly advantageous for administration of agents in accordance with the present invention. Phosphate binding agents, in particular, are intended to be administered orally, usually with meals. The orally administered agents can be can be encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art.

The specific dose can be calculated according to the approximate body weight or body surface area of the patient or the volume of body space to be occupied. The dose will also depend upon the particular route of administration selected. Further refinement of the calculations necessary to determine the appropriate dosage for treatment is routinely made by those of ordinary skill in the art. Exact dosages can be determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

The invention can be further understood by reference to the examples which follow.

EXAMPLE 1

This example illustrates the identification of factors influencing non-enzymatic glycation. The reaction variables studied were phosphate, HEPES, Tris, oxygen, EDTA, light, shaker and excess ribose concentration.

To identify factors involved in non-enzymatic glycation, we performed a fractional factorial experiment in which a model reaction between CBZ-lysine and ribose was investigated in vitro at 37° C. and pH 7.4. The reaction variables were phosphate, HEPES, Tris, oxygen, EDTA, light, shaker, and excess ribose; the responses measured were for changes in pH, $pO_2$, $pCO_2$, fluorescence, and CBZ-L-lysine, and formation of products P1, P2, and P3, as identified on HPLC.

The Na-CBZ-L-lysine-ribose reaction system is based upon Na-CBZ-L-lysine which has a carbo-benzoyl (CBZ) group attached to the alpha amino group of L-lysine. Introduction of CBZ facilitates detection by a UV detector; Na-CBZ-L-lysine is more hydrophobic than lysine and facilitates separation by reverse phase HPLC; and has only the epsilon amino group for reaction. We chose ribose as the reducing sugar for its faster reactivity than D-glucose thereby decreasing the experimental time. The second aspect of our second approach was to use a fractional factorial design. Use of statistical screening designs is often very valuable in investigating complex process particularly the Maillard reaction. We studied the reaction between ribose and Na-CBZ-L-lysine under various reaction conditions. The experimental variables were phosphate buffer, Tris buffer, HEPES buffer, ambient laboratory light, air, ethylenediamine tetra-acetic acid (EDTA), and incubation shaker speed. We monitored the reaction for changes in pH, $pO_2$, $pCO_2$, osmolarity, fluorescence, color formation, consumption of CBZ-lysine, and formation of products as detected on high pressure liquid chromatography (HPLC).

Materials & Met:

Statistical design: Eight experimental variables investigated were phosphate (A), Tris (B), HEPES (C), oxygen (D), ambient laboratory light (E), shaker speed (F), EDTA (G), and ribose (H). We evaluated each variable at two levels. The full factorial design for eight variables, each at two levels, requires a total of $2^8$ or 256 runs. However, as we were interested, initially, in determining only the main effect and their two-factor interactions, we used a $\frac{1}{16}$ fraction of the original 256 run full factorial design. This design was obtained by first writing a full factorial design for three factors in the standard format (see Table I, first three columns A, B, and C, and the top eight rows).

TABLE 1

FRACTIONAL FACTORIAL DESIGN MATRIX

| RUN | PBS | TRIS | HEPES | O2 | Light | Shaker | EDTA | Ribose |
|---|---|---|---|---|---|---|---|---|
| 1 | − | − | − | + | + | + | − | + |
| 2 | + | − | − | − | − | + | + | + |
| 3 | − | + | − | − | + | − | + | + |
| 4 | + | + | − | + | − | − | − | + |
| 5 | − | − | + | + | − | − | + | + |
| 6 | + | − | + | − | + | − | − | + |
| 7 | − | + | + | − | − | + | − | + |
| 8 | + | + | + | + | + | + | + | + |
| 9 | + | + | + | − | − | − | + | − |
| 10 | − | + | + | + | + | − | − | − |
| 11 | + | − | + | + | − | + | − | − |
| 12 | − | − | + | − | + | + | + | − |
| 13 | + | + | − | − | + | + | − | − |
| 14 | − | + | − | + | − | + | + | − |
| 15 | + | − | − | + | + | − | + | − |
| 16 | − | − | − | − | − | − | − | − |

As per convention the negative sign (−) indicates lower limit and the positive sign (+) the upper limit of the variable PBS (0-100 mM), HEPES (0 to 100 mM), TRIS (0 to 100 mM), Oxygen (0, from $N_2$ flush of solution to atmosphere), Light (absent or ambient), Shaker bath speed (zero or 30 rpm), EDTA (0 to 5 mM), Ribose (50 to 100 mM).

Column D was generated from AB, a product of column A and B. The columns D through H were similarly generated as follows: E=BCD, F=ACD, G=ABC, and H=ABD as shown in TABLE 1A.

TABLE 1A

8 Factors: A, B, C, D, E, F, G, H

Factor Generator

E − BCD; F − ACD; G − ABC, H − ABD
Factorial Effects Defining Contrast

I − ABCG = ABDH = ABEF = ACDF = ACEH =
ADEG = AFGH = BCDE = BCFH = BDFG =
BEGH = CDGH = CEFG = DEFH = ABCDEFGH
Factorial Effects Aliases
[Est. Terms] Aliased Terms

[Intercept] = Intercept
Main factor confounded with three factor interactions

[A] = A + BCG + BDH + BEF + CDF + CEH + DEG + FGH
[B] = B − ACG + ADH + AEF + CDE + CFH + DFG + EGH
[C] = C − ABG + ADE + AEH + BDE + BFH + DGH + EFG
[D] = D + ABH + ACF + AEG + BCE + BFG + CGH + EFH
[E] = E + ABE + ACH + ADG + BCD + BGH + CFG + DFH
[F] = F − ABE + ACD + AGH + BCH + BDG + CEG + DEH
[G] = G + ABC + ADE + AFH + BDF + BEH + CDH + CEF
[H] = H + ABD + ACE + AFG + BCF + BEG + CDG + DEF
Two factor interactions confounded with other two factor interactions

[AB] = AB + CG + DH + EF
[AC] = AC + BG + DF + EH
[AD] = AD + BH + CF + EG
[AE] = AE + BF + CH + DG
[AF] = AF + BE + CD + GH
[AG] = AG + BC + DE + FH
[AH] = AH + BD + CE + FG

The remaining eight runs (rows) for all the columns were obtained by "folding over" that is, in the second set of eight rows the signs were all reversed. This resulted in a resolution IV fractional factorial design as shown in Table I. The factorial effects aliases for the main and two factor interactions are shown in Table IA.

The high and low level, indicated by + and − sign respectively, of each variable is shown in Table II.

TABLE II

VALUES OF CODED VARIABLES

| FACTORS | LOW LEVEL (−) | HIGH LEVEL (+) |
|---|---|---|
| Phosphates (mM) | 0 | 100 |
| Tris (mM) | 0 | 100 |
| HEPPES (mM) | 0 | 100 |
| Oxygen (pO2) | $N_2$ flush | Air |
| Light (for 8 Hrs) | 0 | |
| Shaker (rpm) | 0 | 30 |
| EDTA (mM) | 0 | 5 |
| Ribose (mM) | 50 | 100 |

The responses measured were: 1) change in pH, 2) generation of protons, 3) consumption of oxygen, 4) production of carbon dioxide, 5) changes in the relative intensity of fluorescence, 6) consumption of CBZ-lysine, and 7) formation of products P1, P2, and P3 on HPLC analysis. Care was taken to perform the sixteen experiments were performed in random order. Analysis of data required no transformations. The difference between the average responses when the factor is present and absent gives the average effect of each factor over all conditions of the other variables. Due to the general symmetry of the experimental design matrix, there exists a set of eight measures for each response with and without the factor, Thus, the precision of each effect equals to an eight-fold replication over the entire design space. The complete design was once again replicated in random order about six weeks later. Statistical analysis was performed on the complete data that is, the original as well as the replicates. This allowed for the calculation of the pure error terms and had 32 degrees of freedom. Sixteen statistical parameters consisting of one grand mean, 8 main effects each confounded with four three factor interactions, and 7 two factor interactions each confounded with three other two factor interactions were obtained. The half-normal % probability or the full-normal % probability versus effect shows the effect of each variable on the response. Effects that significantly influence the response are away from the normal distribution line and from the 0.0 axis. We developed a statistical linear model by using only significant variables. The statistical parameters of the model were checked for hierarchy prior to analyzing the experimental variance (ANOVA). The sum of squares (SS), degrees of freedom (DF), Mean Square, F value, and probability> F were obtained for the model. Also, various summary statistics for the model, such as square root of the mean square error (Root MSE), R-Squared, adjusted R-squared (Adj. R-Squared), predicted k-squared (Pred. R-Squared), coefficient of variation (C.V.), and predicted residual sum of squares (PRESS) were calculated. We performed post-ANOVA diagnostic checks including scedacity of the variance. Insignificant main or two-factor interactions were deleted until the Studentized residuals were randomly distributed on a normal probability plot (homoscedastic). The responses were also analyzed for any linear or nonlinear correlation between each other and summarized as a correlation matrix consisting of r-squared valves. R-squared valves greater than 0.5 were considered to be significant.

Methods:

All materials used in the study were obtained from Sigma Corp. (St. Louis, Mo.). The buffers were prepared with double distilled water. Eight different experimental variables (continuous) were evaluated. The runs were made in random order (3, 1, 11, 5, 8, 4, 12, 5, 10, 2, 7, 9, 6, 14, 16, and 13). Two ml of each solution was prepared and pH was adjusted to 7.4. Solutions were filtered through 0.22-micron filters, divided into each of two sterile 10-ml serum vials, and sealed with an airtight rubber septum and aluminum cap. Thus each solution was 1 ml and was contained in a 10-ml serum vial. Solutions which needed to have low $O_2$ had sterile-filtered nitrogen gas bubbled through the solution for 5 minutes. All solutions were placed in a water bath at 37° C. for a period of one week; samples 1, 2, 7, 8, 11, 12, 13, and 14 were continuously shaken at 30 rpm while the remaining were kept stationary. Eight samples: 1, 3, 6, 8, 10, 12, 13, and 15 were wrapped with aluminum foil to minimize exposure to ambient laboratory light. Samples were checked visually as well as plated on agar culture plates to check for microbial growth. An aliquot of the reaction mixture was withdrawn from the serum vial without introducing any air and it was injected into the blood gas analyzer (Blood gas Corning 170 pH/blood gas analyzer), and the pH, $PO_2$, and $pCO_2$ recorded. Air was saturated with water vapor at ambient barometric pressure. The pH of the sample was also measured using a stand-alone pH meter (Fisher Accumet model 25). Fluorescence absorption measurement was made by diluting (10-50 fold) the sample with phosphate A C buffered solution (pH 7.4) using an excitation wavelength of 370 nm and measuring the emission at 430 nm (Perkin-Elmer LS-5D Luminescence Spectrometer). The HPLC condition for analysis of samples was as follows: c-IS stationary phase of 5.0 um particle size packed in a column of diameter 4.6 mm and length of 250 mm. The mobile phase was a mixture of acetonitrile (90% containing 0.1% trifloro-acetic acid) and water (10%). The products in the eluent were detected by monitoring its absorbency at 254 nm and 295 nm using a Waters 490E-programmable multiwavelength detector. As the samples had different buffering capacity, depending on the combination of buffers and reactants, the amount of $H^+$ needed for a unit change of pH was different for each sample combination. Therefore, a calibration curve was obtained for each combination of buffer solution by titrating with 0.1N HCl and noting the change in pH.

We determined the trace metal content of the reagents using ICP-MS technique. Typically 0.1 gm of the reagent was dissolved in 100 ml of 1% $HNO_3$ acid. An internal standard of In (10 ppb) was added and the samples were analyzed a series of certified reference standards and heated to evaporation. The residue was redissolved in water and an aliquot was injected into the ICP-MS. The spectrum was analyzed for Cu, Fe, Cr, Zn, Mn, V, Ni, and Co, based on known internal standards. Samples were run in triplicates.

Results:

As our experiment had eight variables and nine responses, we discuss the effect of all the variables on each response as well as the effect of each variable on all the responses.

Figure 1B:
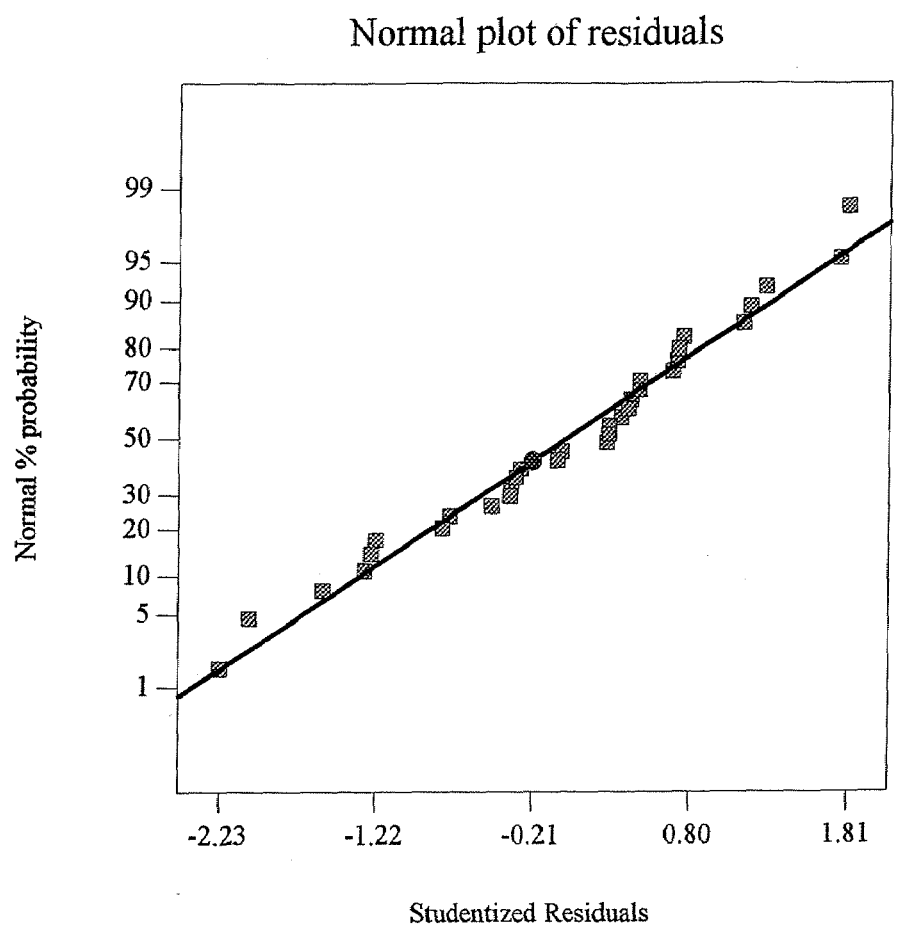

Effect of variables on change in pH: Maximum and minimum decrease in pH was observed in run #4 ($\Delta pH=-1.23$) and #12 ($\Delta pH=-0.02$) respectively. FIG. 1A is a normal % probability plot of factors that influence pH. Main factors A, C, D, G, and H were significant in changing the pH with factor C increasing the pH. Among the two-factor interactions AB, AD, AF were found to be significant. The statistical significance of the linear model and for the factors is shown in Table IA. The effect of AB and AF were confounded by DH and CD. To confirm that phosphate, HEPES, oxygen, EDTA, and ribose were responsible for the effect and not their confounding terms (see Table IA) the insignificant factors light, shaker, and Tris, in this case, were deleted. The data was reanalyzed with the remaining factors as a half-factorial design with less confounding terms. Phosphate, oxygen, ribose, HEPES, and EDTA were observed to be unambiguously significant and in decreasing order. HEPES and EDTA increased the pH. The two-factor interaction was confirmed to arise from interactions between phosphate-oxygen, oxygen ribose, and oxygen-HEPES. The three and four factor interactions were insignificant. The p>F and R-Sqd. value for the half-factorial model were 1.13E-10 and 0.92 respectively and the post-ANOVA statistics were very good with the expected random distribution of Studentized residuals on a normal plot shown in FIG. 1B. The final equation in terms of the coded factors that were significant is shown below as well as in Table III, column 2.

$$\Delta pH=-0.36-0.17*PBS-0.16*pO_2-0.12*ribose+ 0.11*HEPES+0.047*EDTA-0.09*PBS*pO_2- 0.10*pO_2*ribose+0.044*HEPES*PO_2 \quad (1)$$

TABLE III

STATISTICAL SIGNIFICANCE FOR THE LINEAR MODEL (P > F) AND FOR THE FACTORS (P > T) FOR EACH OF THE RESPONSES

| | pH | H+ | PO2 | PCO2 | Fluorescence | CBZ-Lysine | P1 | P2 | P3 |
|---|---|---|---|---|---|---|---|---|---|
| Model | 2.08E−13 | 1.84E−18 | 1.33E−05 | 8.47E−12 | 4.28E−19 | 4.45E−04 | 1.51E−02 | 1.017E−02 | 6.36E−02 |
| R-sqd. | 0:9576 | 0.9802 | 0.8559 | 0.9460 | 0.9820 | 0.8531 | 0.7455 | 0.7592 | 0.6712 |
| A: PBS | 4.13E−08 | 1.67E−12 | 9.53E−07 | 2.11E−07 | 2.88E−14 | 2.22E−06 | 3.83E−05 | 1.04E−02 | 1.10E−02 |
| B: TRIS | 3.75E−01 | 5.41E−06 | 4.06E−02 | 5.01E−01 | 3.9E−04 | 2.21E−01 | 3.72E−01 | 4.04E−02 | 6.53E−01 |
| C: HEPPES | 7.08E−06 | 4.79E−02 | 7.04E−01 | 4.73E−01 | 2.67E−03 | 5.03E−02 | 7.94E−01 | 4.71E−01 | 2.12E−01 |
| D: Oxygen | 1.01E−07 | 3.70E−09 | 2.73E−03 | 1.04E−07 | 6.93E−04 | 1.01E−02 | 9.84E−02 | 3.61E−03 | 3.00E−03 |
| E: Light | 2.65E−01 | 4.82E−01 | 1.45E−01 | 3..51E−02 | 5.62E−04 | 2.24E−01 | 2.25E−01 | 7.34E−02 | 5.49E−01 |
| F: Shaker | 1.66E−01 | 1.34E−01 | 4.58E−01 | 3.41E−01 | 1.23E−02 | 8.69E−02 | 6.49E−01 | 4.08E−01 | 6.95E−01 |
| G: EDTA | 1.47E−02 | 4.35E−01 | 3.86E−02 | 6.42E−03 | 2.40E−04 | 1.17E−01 | 2.47E−01 | 7.47E−01 | 7.76E−01 |
| H: Ribose | 2.74E−06 | 3.60E−07 | 2.97E−02 | 3.95E−01 | 5.10E−06 | 1.40E−02 | 5.04E−01 | 1.04E−01 | 9.04E−01 |
| 11 | 1.71E−05 | 1.58E−04 | 2.41E−01 | 5.23−02 | 2.07E−03 | 3.85E−01 | 4.92E−01 | 2.54E−01 | 7.81E−01 |
| 12 | 1.98E−01 | 1.70E−01 | 3.64E−01 | 3.05E−01 | 6.94E−01 | 4.38E−01 | 6.38E−01 | 7.62E−01 | 5.84E−01 |
| 13 | 9.97E−05 | 3.71E−08 | 2.04E−01 | 2.50E−07 | 3.29E−03 | 4.03E−01 | 1.43E−01 | 3.13E−02 | 1.50E−02 |
| 14 | 1.51E−01 | 5.43E−02 | 8.32E−01 | 1.30E−03 | 3.05E−06 | 1.08E−01 | 1.60E−01 | 3.97E−01 | 8.99E−01 |
| 15 | 2.00E−02 | 5.00E−01 | 5.43E−01 | 9.82E−01 | 4.49E−02 | 2.36E−01 | 8.06E−01 | 8.46E−01 | 2.71E−01 |
| 16 | 1.03E−01 | 9.68E−01 | 6.50E−01 | 6.22E−03 | 2.61E−03 | 2.98E−01 | 1.76E−01 | 1.88E−01 | 6.51E−01 |
| 17 | 6.73E−02 | 9.60E−06 | 7.23E−01 | 9.82E−02 | 3.22E−03 | 6.62E−02 | 6.45E−01 | 1.36E−02 | 5.45E−01 |

Figure 1C:
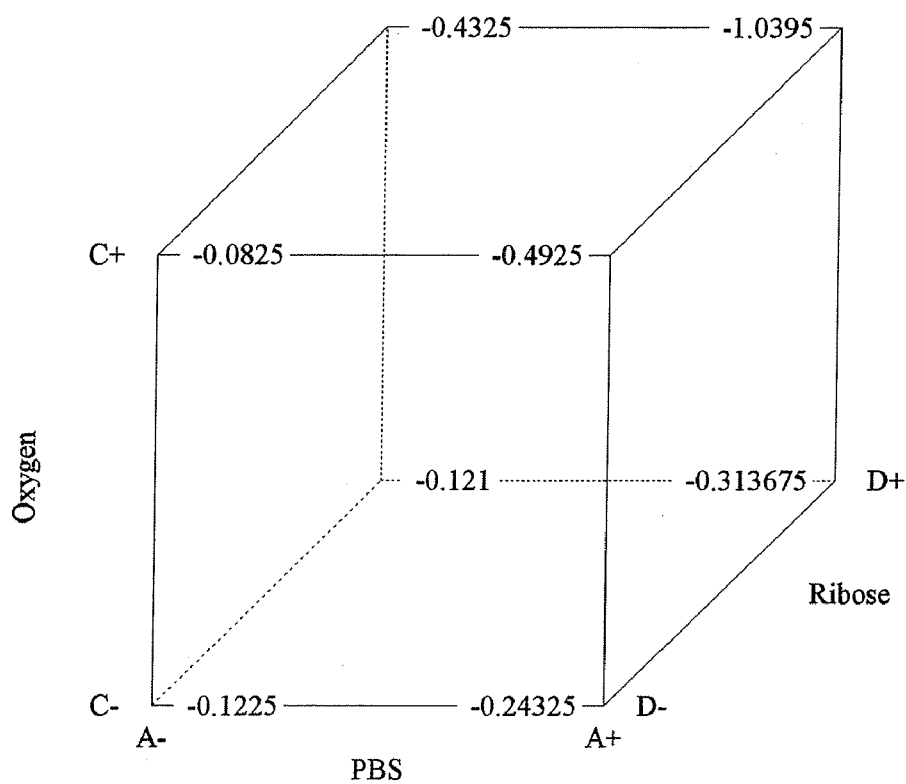

As oxygen interacts with phosphate and ribose to influence the pH of the reaction mixture, it is not possible to interpret its effect individually. Therefore, the interactions of oxygen with phosphate and ribose are shown in FIG. 1C as a cubic plot.

Figure 2A:
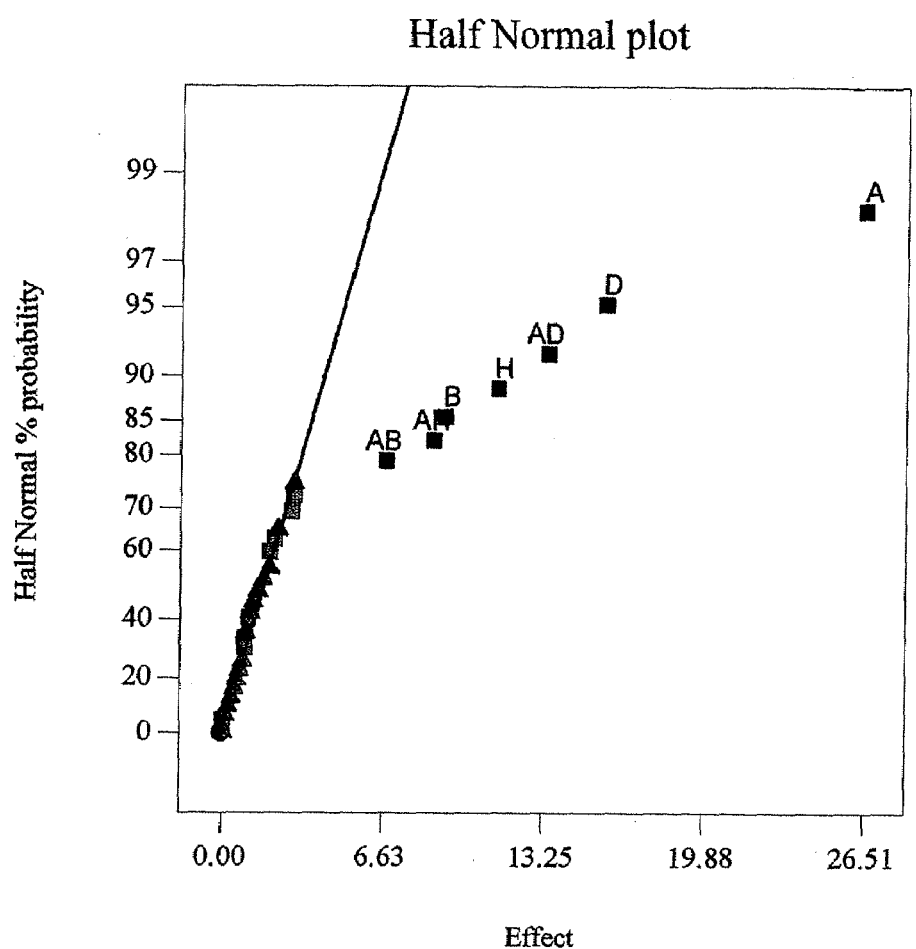
FIG. 2 illustrates (A) the half-normal % probability plot of the various factors and their two-factor interactions on the amount of protons generated, (B) the main effect of phosphate, oxygen, and ribose along with their two and 3-factor interaction shown as a cubic plot, and (C) a combined contour and surface plot of the interaction between phosphate and ribose, mathematically computed, with $pO_2$ and EDTA at the "high level" and the rest of the factors at the "low level."
Figure 2B:
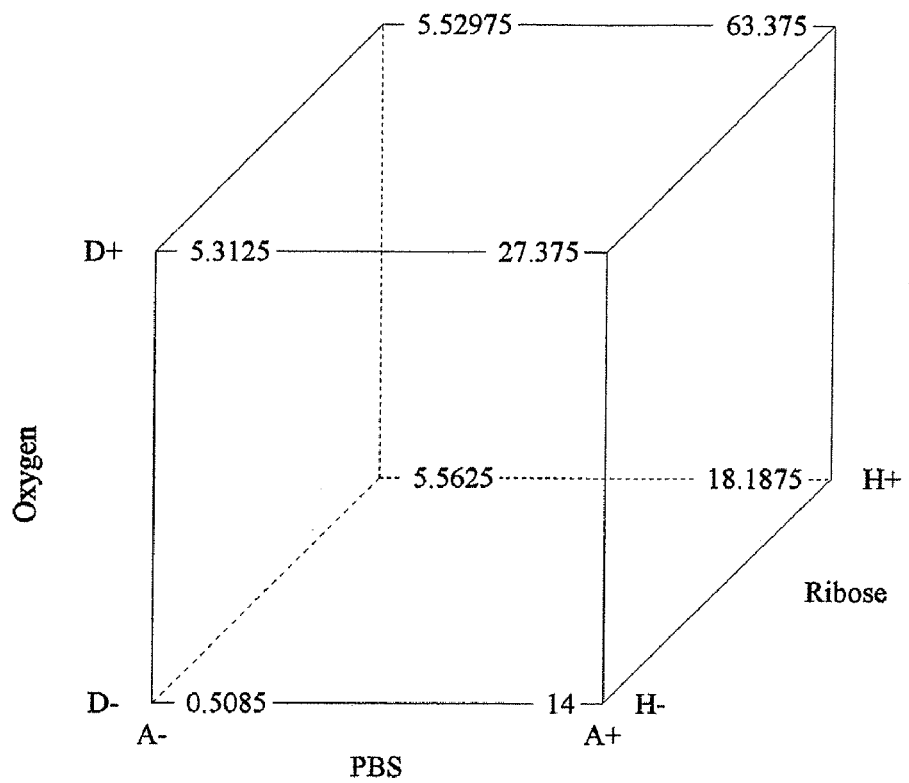

Effect of variables on protons formed: As the buffering capacity of the various runs (mixtures) were different, the change in pH was equated to the amount of H+ produced by using a calibration curve as described in the methods section, The values are based on titrating a 20 ml buffer solution. Run #8, which had all three buffers, produced the maximum amount of protons (73 mEq. corresponding to a $\Delta pH=- 0.907$). Minimum amount of $H^+$ (0.01 mEq.) was produced in run #16 which had all the factors at the 'low level' (see Table II). The half-normal % probability plot of the various factors and their two-factor interactions on the amount of protons generated is shown in FIG. 2A. Factors A, B, C, D, and H were significant in producing $H^+$. Among the two factor interactions AB, AD, and AH were significant (see FIG. 2A). Table III, column 2 shows the statistical significance and R-Sqd. for the linear statistical model, and the significance of the main factors and their two-factor interactions. The estimate of coefficients for only the significant factors, in coded values, is shown in Table IV column 2. As A, D, H, AD, and AH were very significant, it was unclear if the influence of factor B on production of $H^+$ was from Tris or from the three-factor interaction of ADH. Therefore, the data was reanalyzed, after deleting insignificant factors (factors C, E, F, and G), as a full three factorial design with phosphate, oxygen, and ribose, as well as a four factorial design that included Tris. From such analysis, we confirmed that the 3-factor interaction, ADH, influenced the formation of $H^+$ rather than Tris. The p>F for the 3-factor linear model was 1.99E-15 and the R-Sqd. was 0.96. The main effect of phosphate, oxygen, and ribose along with their two and 3-factor interaction is shown in FIG. 2B as a cubic plot. The front left corner represents the amount of $H^+$ (0.5085 mEq.) formed in the reaction mixture at the end of the incubation period when phosphate, oxygen, and ribose are at the 'low level'. The back right upper corner (63.37 mEq.) represents the effect when all three factors are present at their 'high level'. The final equation for the production of protons, in coded form, is given by equation (2).

$$\Delta[H+]=17.39+13.25*PBS+7.92*PO_2+5.68*ribose+ 6.72*PBS*PO_2+4.36*PBS*ribose+ 337*pO_2*ribose+4.58*PBS*pO_2*ribose \quad (2)$$

Figure 2C:
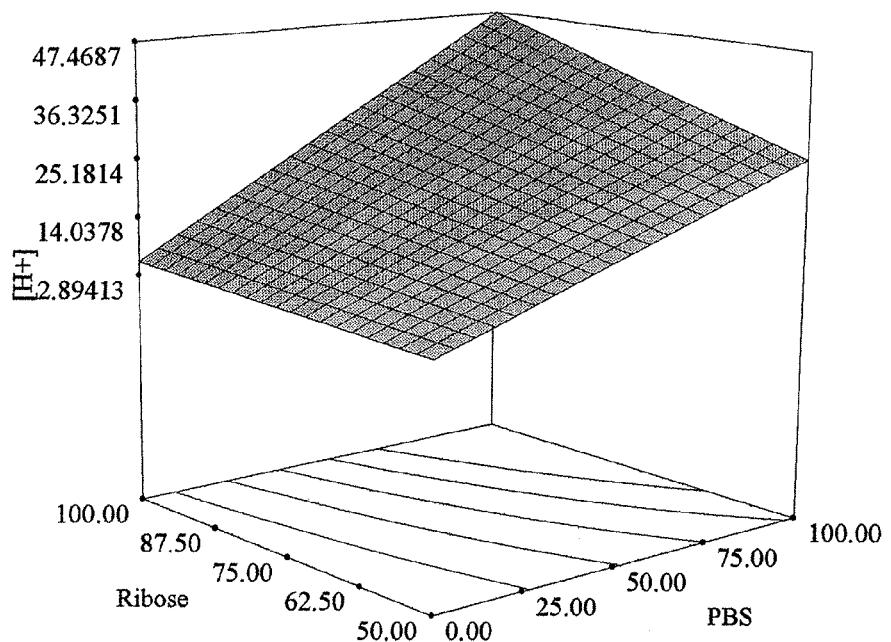

FIG. 2C shows a combined contour and surface plot of the interaction between phosphate and ribose, mathematically computed, with $pO_2$ and EDTA at the 'high level' and the rest of the factors at the 'low level'.

Effect of variables on consumption of $pO_2$: Solutions that were purged with nitrogen for five minutes showed an average $pO_2$ of 55 mm of Hg, the rest had an average $pO_2$ of 188 mm Hg. The change in $pO_2$ (mm of Hg) ranged from -117.7 to +41.7 with the mean being -36.12. Phosphate ions and probably oxygen were the only significant variables that affected the consumption of $pO_2$. In general, the partial pressure of oxygen was noted to decrease at the end of the incubation period. In runs #2, 6, 9, and 13, the incubation mixture became anaerobic. The common features in these runs were the presence of phosphate at the 'high level' and oxygen at the 'low level'. In two runs (#7 and #16,) there was a significant, consistent, and reproducible increase in the partial pressure of oxygen indicating that oxygen was formed during the incubation period. Runs #7 and #16 were significant for the absence of phosphates, light, and EDTA, and low levels of oxygen and a relatively low value in all the observed responses. The linear statistical model had a value of 1.43E-07 and an R-Sqd. of 0.82. There was no significant interaction between phosphate and oxygen in the consumption of oxygen. The linear model representing the consumption of oxygen in coded factors is given below $$-\Delta pO_2=-36.12-27.37*PBS-12.63pO_2-8.52*ribose- 8.04*EDTA \quad (3)$$

Effect of variables on $pCO_2$: The partial pressure of carbon dioxide (pCO2) increased in all the runs. The maximum average increase of 21.6 mm was observed in run 8, and the least change (0.2 mm) was seen in run 16. The average increase in $pCO_2$ was 5.6 mm, In runs #8 and #16, all factors were at the 'high level' and 'low level' respectively. The statistical linear model was significant at p=5.50E-1 I and its R-sqd. was 0.9225 (see Table III).

Again, oxygen, phosphate, and their interaction had the greatest influence in the formation of carbon dioxide (p<1.00E-06). EDTA (p<0.0046) and Light (p<0.0309) were also noted to have an effect on production of carbon dioxide. Interestingly, ribose was not significant in influencing the $pCO_2$. The estimate of coefficients for significant factors is given in Table IV.

TABLE IV

THE ESTIMATE OF COEFFICIENTS OF FACTORS THAT SIGNIFICANTLY INFLUENCE EACH RESPONSE

|  | pH | H+ | PO2 | PCO2 | Fluorescence | CBZ-Lysine | P1 | P2 | P3 |
|---|---|---|---|---|---|---|---|---|---|
| Intercept | -0.356 | 17.481 | -36.119 | 5.259 | 223.031 | 9.234 | 0.178 | 0.023 | 0.033 |
| A: PBS | -0.166 | 13.253 | -27.375 | 3.4781 | 189.612 | 5.833 | 0.171 | 0.017 | 0.026 |
| B: TRIS |  | 1.581 |  |  | 30.263 |  |  |  |  |
| C: HEPPES | 0.112 |  |  |  |  |  |  |  |  |
| D: Oxygen | -0.156 | 7.917 | -12.63 | 3.666 | -28.375 | 2.373 | -0.054 | 0.020 | 0.032 |
| E: Light |  |  |  |  | 29.044 |  |  |  |  |
| F: Shaker |  |  |  |  |  |  |  |  |  |
| G: EDTA |  |  |  | 1.266 | 31.142 |  |  |  |  |
| H: Ribose | -0.121 | 5.682 |  |  | 45.325 |  |  |  |  |
| 11 | -0.104 | 3.372 |  |  |  |  |  |  |  |
| 12 |  |  |  |  |  |  |  |  |  |
| 13 | -0.088 | 6.724 |  | 3.434 |  |  |  |  |  |
| 14 |  |  |  | 1.572 | 47.300 |  |  |  |  |
| 15 |  |  |  |  |  |  |  |  |  |
| 16 |  |  |  | 1.272 |  |  |  |  |  |
| 17 |  |  | 4.365 |  |  |  |  |  |  |

The final equation of $pCO_2$ in terms of coded factors is shown in equation 4.

$$\Delta pCO2=\pm5.26+3.48*PBS\pm3.67*pO_2+1.27*EDTA+ 3.43*PBS*pO2+1.57*PBS*light+ 1.27*PBS*EDTA \quad (4)$$

Figure 3A:
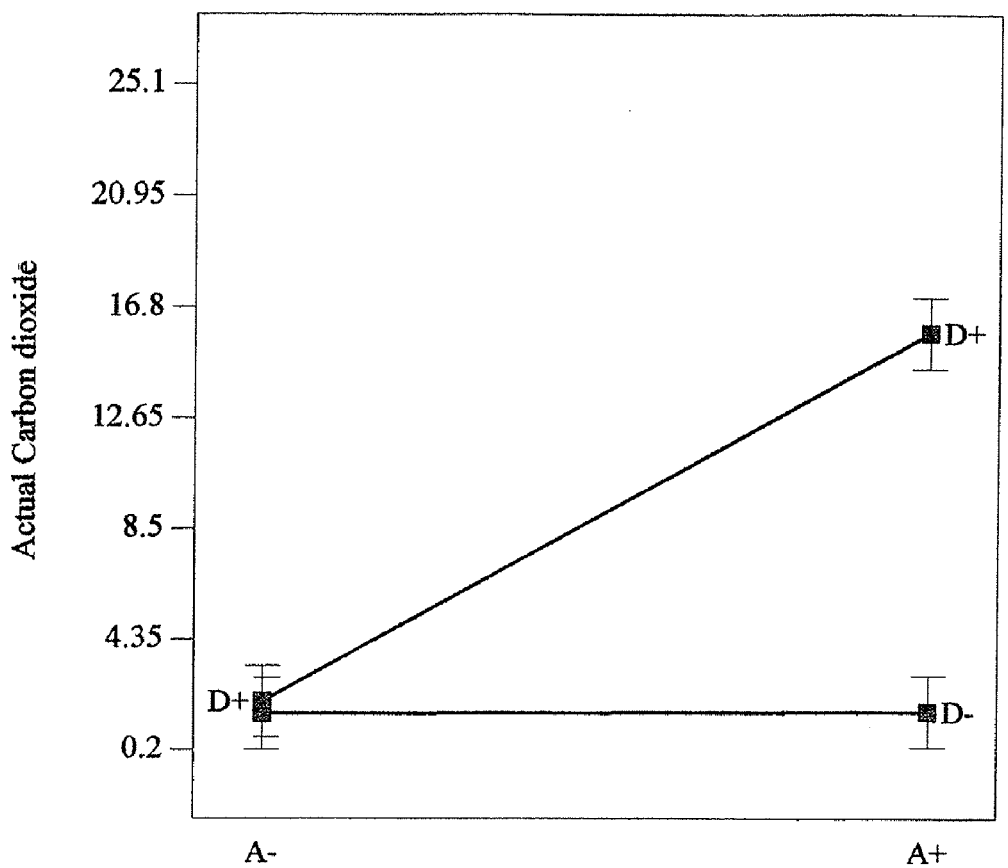
FIG. 3 illustrates the two-factor interaction plots between phosphate and (A) oxygen, (B) light, and (C) EDTA.
Figure 3B:
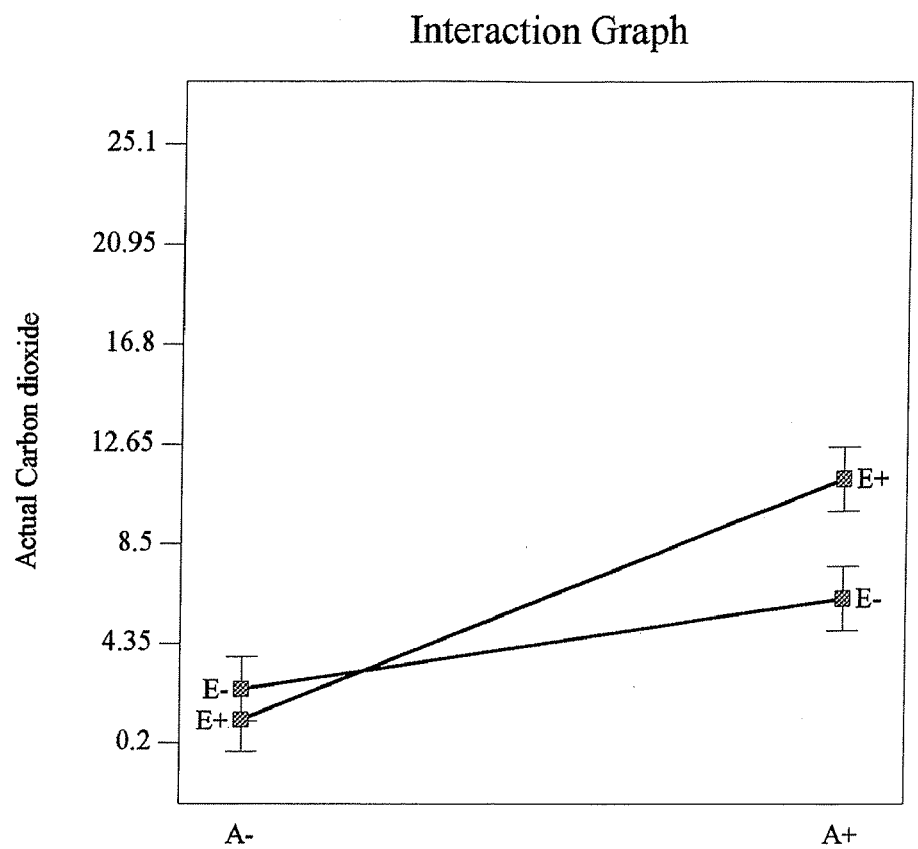
Figure 3C:
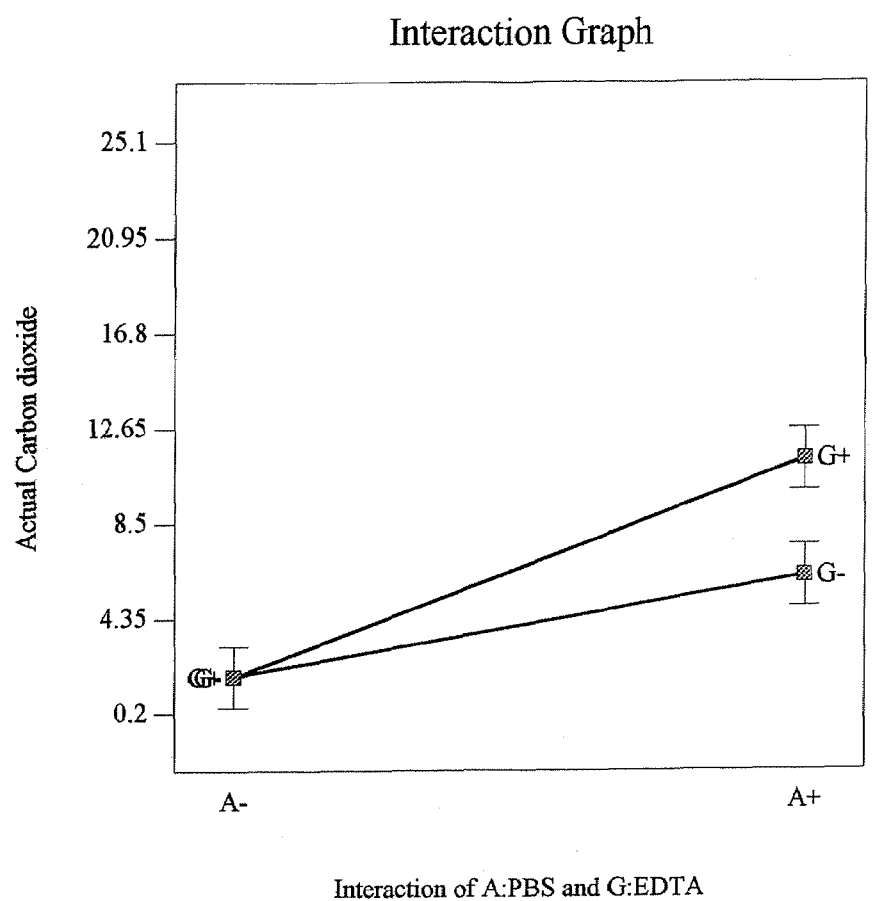

The two-factor interaction plots between phosphate and oxygen, light, and EDTA are shown in FIGS. 3A, 3B, and 3C respectively.

Figure 4:
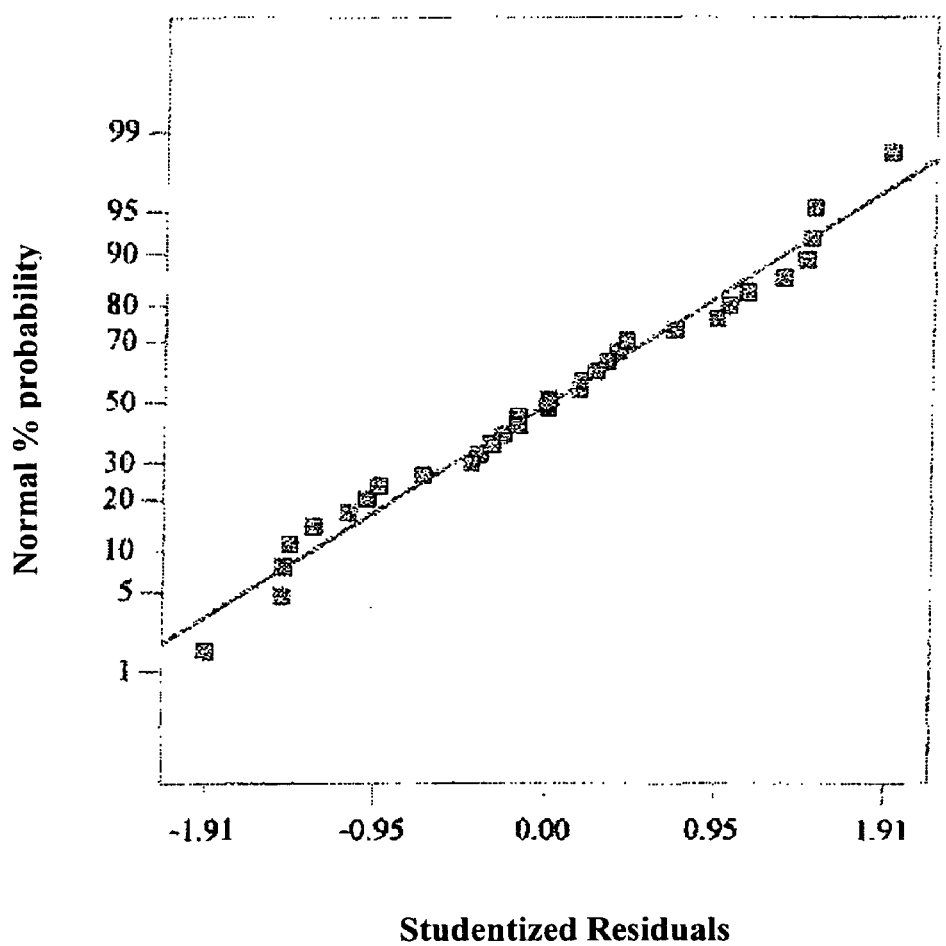
FIG. 4 illustrates the normal % probability plot of the Studentized residuals.

Effect of variables on fluorescence: The fluorescence response was influenced by many variables. Runs #6 and #8 fluoresced considerably while runs #1, #10, and #14 exhibited minimal fluorescence. The statistical linear model was significant at 'p>F' 5.60E-12 with an R-Sqd. of 0.9819 (see Table III). FIG. 4 shows the normal % probability plot of the Studentized residuals. Table III shows the statistical significance of all the factors in the model; and Table IV shows the estimate of coefficients of significant factors only. Tris and oxygen showed a significant negative influence on fluorescence and shaker bath speed had the least effect. The rest of the factors exhibited varying degrees of significance. Interestingly, there was a significant interaction between phosphate-light, and phosphate-EDTA. In the absence of phosphate light has minimum effect however, in the presence of phosphate light significantly increases fluorescence. It should be pointed out that the fluorescence studies were performed at only a single excitation/emission wavelength.

$$\text{Fluor} = 223.03 + 169 \cdot PBS + 47.3 \cdot PBS \cdot \text{light} + 45.33 \cdot \text{ribose} + 31.14 \cdot EDTA - 30.26 \cdot Tris + 29.04 \cdot \text{light} - 28.38 \cdot pO_2 \quad (5)$$

Effect of variables on the consumption of CRZ-Lysine: The reaction consumed CBZ-lysine during the incubation period with the maximum consumption being 24% in run #8. Only phosphate, oxygen, and ribose significantly influenced this consumption. No interactions between variables were observed. The model was significant at p>5.40E-06 and the equation is given below $$\Delta CBZ\text{-lysine} = 9.23 + 5.83 \cdot PBS + 2.37 \cdot pO_2 + 2.24 \cdot \text{ribose} \quad (6)$$

Effect of variables on the formation of products P1, P2, and P3: Three major products were identified based on HPLC analysis and labeled as P1, P2 and P3. Not all three products were present in all the runs and their amounts varied. The chemical identity of these products is not known. Phosphate influences the formation of all three products while oxygen is associated with form P2 and P3 only. PBS*$O_2$ interaction played a significant role in the formation of P2 and P3 while PBS*ribose influenced the formation of P2.

Effect of each variable on the responses: In the above section, the effect of variables on each response was summarized. Here we briefly summarize the effect of each variable on the responses. Only phosphate significantly influenced all responses and this trend was followed closely by oxygen. Tris decreased $pO_2$ and fluorescence formed. HEPES mainly increased pH and fluorescence. Ambient laboratory lighting increased $pCO_2$, fluorescence, and formation of P2. EDTA was associated with increase in pH, consumption of oxygen, formation of carbon dioxide, and fluorescence production. Ribose significantly altered pH, protons formation, oxygen consumption, and fluorescence production. Speed of the shaker did not influence on any of the responses investigated.

Among the factor interactions PBS-oxygen interaction influenced pH, $H^+$, $pCO_2$, fluorescence, P2, and P3. PBS-light interaction affected formation of carbon-dioxide and fluorescence. PBS-EDTA interacted to enhance formation of carbon-dioxide and fluorescence. PBS-ribose interaction was associated with formation of protons, fluorescence, and P2.

Correlation of responses on each other: In the above paragraphs the effect of experimental variables on responses were described and here we report the relationship between responses. As there are eight responses, there are 36 combinations of response pairs. Correlation between responses is important to provide mechanistic insight in this complex reaction. In general, the amount of protons generated correlated better than pH with all the responses. [$H^+$] was substantially associated (r-sqd>0.5) with consumption of oxygen and CBZ-lysine, and formation of $CO_2$, fluorescence, and P2. CBZ-lysine was strongly associated with fluorescence formation. P1 was also associated with fluorescence while P2 and P3 were not and P3 seems to be related to P2.

Discussion:

Statistical Model: Traditionally, one estimates the influence of experimental variables using the "one-factor-at-a-time" while keeping the other variables at some arbitrarily chosen constant value. In such a technique, one assumes the effect of a variable to be the same at all other variable levels and that the variables act only additively. In contrast, the factorial design helps determine the effect of a factor over a complete range of other variables, with greater precision, and accounts for nonadditive interactions. In general, initially examining a factor at two levels is efficient and economical. Therefore, to evaluate eight variables at two levels a full factorial design would consist of $2^8$ or 256 experiments. This technique elucidates the main effects and all of the possible two, three, and higher level interactions unambiguously. Although the full factorial design has considerable advantages over the one-factor-at-a-time, in practical terms, even the full factorial design has some redundancy. In terms of the magnitude generally, the main effects tend to be larger than the two-factor interactions, which in turn tends to be larger than the three factor interactions, and so on. The partitioning of each type of p-factor interactions in a $2^f$ design is given by the following equation $$\frac{f!/(f-p)}{p!}$$

Thus the 256 statistics is partitioned between 1 mean, 8 main effects, 28 2-factor interactions, 56 3-factor interactions, 70 4-factor interactions, 56 5-factor interactions, 28 6-factor interactions, 8 7-factor interactions, and 1 8-factor interaction. For quantitative continuous variables, as in our case, the higher order interactions tend to be negligible and can be disregarded. In addition, in a higher order full factorial design of five or more variables, all variables may not be significant. In other words, some variables would be relatively insignificant and simply add to the "noise" of the system. Thus, only a fraction of the original lull factorial run of experiments will contain the "signal," Fractional factorial designs have the ability to extract the "signal" efficiently in fewer experiments by taking advantage of this redundancy. Thus, fractional factorial designs are excellent for screening a large number of variables. As our initial goal was to identify the effect of the main factors independent of other main effects, and their two-factor we chose a resolution IV fractional factorial design. This design uses only 1/16 of the full factor design, the main effects are independent of each other but confounded with seven 3-factor interactions, and the two factor interactions are confounded with three other 2-factor interactions. We assumed that not all the factors would be significant for all the responses. Therefore, after deleting the insignificant factors the data could be reevaluated less ambiguously. In addition, one could use chemistry insight to verify statistical results.

If the effects represent a sample from a normal distribution, we would expect to see them form a straight line on a % normal probability plot of the effects. Usually, only a few effects turn out to be important which show up as outliers on the % normal probability plot. The % half-normal probability plot follows the same principle as the full % normal probability plot except that the sign of the effects is ignored in plotting. Thus, large absolute values show up as outliers in the upper right-hand corner of the graph. The line for the half-normal plot should start from the origin and go through the set of near-zero effects. The effect of factors on each response was analyzed using both probability plots. H In the half-normal probability plot, insignificant effect will be near zero, scattered in a normal distribution. That is, significant effects fall to the right of the line and away from zero. Replicates provide an independent estimate of pure experimental variability or error over the design space. The pure error estimate is used for evaluation of statistical significance. On a normal probability plot, pure error points should fall on a line coincident with insignificant effects.

Mechanistic Model:

As mentioned in the introduction section, our initial intention was two folds, first to determine which of the experimental variables maximally influenced the NEG reaction under in vitro physiological conditions and second to determine the causes of irreproducibility of cited literature, Based on conventional wisdom that sustained hyperglycemia is strongly associated with long-term complications, we anticipated ribose to be the most significant variable influencing fluorescence. We were also aware that buffers influence the extent of glycation under in vitro conditions and that phosphate buffer reacts poorly with radicals while organic buffers such as Tris and HEPES scavenge reactive intermediates. In addition, phosphates had a greater effect glycation, among the buffers. The effect of phosphate has been traditionally attributed to the presence of adventitious trace metals that can catalyze this reaction even at micromolar concentrations. Thus, the use of metal chelators has been advocated to inhibit the catalytic effect of trace metals. We therefore anticipated EDTA to considerably reduce fluorescence. As the reaction is not diffusion controlled, we did not expect the speed of the shaker to have any effect nor did we anticipate low-level (50 ft/candles) of ambient laboratory light to affect any response. As indicated in the results section, the chemometric analysis revealed several interesting features. Phosphates significantly modulate this reaction more than excess ribose under the present experimental conditions. There is a considerable change in pH of the solution in spite of being buffered. Experiments that had normal tension of oxygen at the beginning of the reaction were rendered anaerobic with high $pCO_2$. In some cases in which the solution was purged with nitrogen, the reaction produced oxygen. EDTA did not inhibit fluorescence formation. Also, several interactions between variables were observed and trace metal analysis indicated that CBZ-lysine was the main source of adventitious trace metals, Based on these observations we believe that the sources of irreproducibility arise from lack of experimental details to the dead space in the container, the partial pressure of oxygen, the amount of adventitious trace metals in the reagents, the intensity and duration of ambient laboratory light. In the following paragraphs, we have attempted to explain some of our observations based on information obtained from the literature.

Acid forming reactions: Among the variables phosphate, oxygen, and ribose strongly affected the formation of protons; and among the responses, the consumption of CBZ-lysine and formation of carbon dioxide were associated with production of acidity. This suggests that acidic group may result from the oxidation of ribose, consumption of CBZ-lysine. HCl with liberation of HCl, and formation of carbon dioxide.

D-ribose, in solution, exists in six tautomeric forms: α- and β-pyranose, α- and β-furanose, the open chain aldehyde, and its hydrated form. The β-pyranose form predominates in solution at 37 C and pH 7.0 (Cortes, 1991). The ratio of the hydrate to aldehyde in solution is approximately 10:1 (Angyal, 1984) and the two forms represent less than 1% of the tautomers. Ribose like other a-hydroxy aldehydes, forms an enediol anion in neutral or basic conditions. The enediol anion is an essential intermediate in the Lobry de Bruyn-Alberda van Ekenstein transformations give hydroxy-carboxylates. Only the acyclic form enolizes and may undergo β-elimination, direct oxidation by oxygen, or concomitant degradation, e.g., C—O or —C—C bond fission. Smith and Thornalley observed that the enolization of monosaccharides and its subsequent oxidation to ketoaldehyde, an α-dicarbonyl, in presence of air is associated with hydrogen peroxide. In principle, hydrogen peroxide detected during the formation of dicarbonyl sugars may be consumed in other oxidative reactions. For example, α-hydroxy acids and α-keto acids are cleaved by hydrogen peroxide with a-hydroxy acids giving aldehydes or ketones, and α-keto acids generating acids (March pg. 1087). This degradation step by hydrogen peroxide, of ahydroxy acids, when catalyzed by iron ($FeSO_4$) is known as Ruff degradation and is used extensively to elucidate the structure of sugars.

In addition to ribose, other chemical intermediates such as Schiff-base, carbinolamine, and Amadori product could be oxidized or generate acidic by-products (Stadtman, 1952; Katchalsky, 1953). Ahmed et al, (Ahmed, 1986) from their studies on glycated proteins and fructosyl-lysine a model Amadori product, have identified N-carboxymethyllysine (CML) and erythronic acid as a product of glycoxidation; the reaction requires oxygen and trace metals catalyze it. Analogous reaction with ribose-CBZ-lysine would also result in generation of protons and a decrease in pH. Scheme I shows the above possible reactions that may produce acidic groups.

Effect of oxygen: The initial oxygen pressure in solutions that were not purged with nitrogen varied. The solubility of oxygen in pure water is given by Benson and Krause (Benson, 1982) and its solubility in aqueous solutions containing different ions is given by $$\log(He/He_0) = 0.5 \sum_i H i z_i^2 C_i$$

Where $He$, $He_0$ are the Henry coefficient in aqueous ionic solution and pure water respectively. Henry coefficient is the ratio of the partial pressure of a gas and its equilibrium concentration in the liquid, Hi is the salting-out parameter, z the ion charge, and C the concentration of species i. As the solutions had different concentration of buffers and no attempt was made to keep the ionic strength of the reaction constant, the initial partial pressure of oxygen varied by about 10%.

The reactivity of oxygen is characterized by its electronic configuration. Oxygen has considerable affinity for electrons, as evidenced by the fact that most oxidation reactions involving oxygen are exothermic. Molecular oxygen, or dioxygen, under ambient conditions is kinetically stable. The origin of this stability is due to the distribution of two obits valence electrons in a ground-state triplet ($T_0$), $^3\Sigma_g^-$ (unpaired), in which the electrons are distributed in the degenerate pair of antibonding r*-orbitals. As the two electrons are in planes 90° apart, dioxygen behaves as a biradical and may only participate in singlepoint attack radical-like reactions. Since most organic molecules usually have paired electrons and are in singlet ground states, their reaction with dioxygen triplet ground-state C, is spin forbidden. This kinetic sluggishness can be circumvented by one of three ways: 1) reacting the triplet with a radical to form peroxyl radical 2) complexing with a paramagnetic metal ion, or 3) exciting the triplet to one of its two low-lying singlet states (Si and S2). In S1 ($^1\Delta_g$) the electron spins are paired and may lie parallel or perpendicular to each other leaving the other π* 'empty'. Due to this positional variation, the $S_1$ oxygen can participate as a single-point radical or in concerted addition reactions with a two-point attack, or as an electrophile via its empty orbital. In S2 state and energetically higher of the two ($^1\Sigma_g^+$), the electrons are forced to be coplanar in spatial disposition, and could be expected to participate only in two-point concerted addition reactions. The first two pathways are not spin restricted, and the third pathway usually occurs photochemically. Under biological conditions, oxygen is reduced to superoxide, hydrogen peroxide, hydroxyl radical and water via a 4-electron reduction. Transition metals facilitate this reduction process. The overall reaction may be written as $$4Fe(II)+O_2+4H^+ \rightarrow 4Fe(III)+2H_2O$$

Under our experimental conditions the consumption of oxygen is significantly influenced by phosphates, (see Table III) and is associated with formation of carbon dioxide and consumption of CBZ-lysine (see Table V). However, ambient laboratory light had no significant effect. Thus, the consumption of oxygen may be largely proceeding via triplet state rather than as a singlet oxygen with the reaction being initiated by trace or adventitious transition metal and later by free radicals generated during the reaction. Under conditions simulating physiological environment, Spoehr (Spoehr, 1934) observed that oxygen reacts with trioses, in the absence of amino acids but in the presence of sodium ferropyrophosphate-phosphate mixtures, to produce carbon dioxide. Clinton observed that phosphate or arsenate catalyze the reaction, and the rate depends on concentration of salt present, but not as much on pH (Clinton, 1937). Traube (Traube, W. 1936) observed that salts of copper, cobalt, iron, and nickel also catalyzed the consumption of oxygen formatting carbon dioxide and formic acid. Oxygen may also be consumed in oxidizing the Amadori product for example in the formation of carboxymethyl-CBZ-lysine (Scheme II). In two different experiments (runs #7 & 16) $pO_2$ was greater at the end of the incubation period. In other words oxygen was formed. Runs #7 and #16 were significant for the absence of phosphates, light, and EDTA, and low levels of oxygen. Trace metals are present in CBZ-lysine probably as a complex, and if the redox potential is significantly decreased the system may oscillate with water being oxidized and oxygen being reduced.

Formation of Carbon dioxide: As mentioned previously, one source of carbon dioxide is the oxidation of ribose. However, in the presence of amino acids. Stadtman (Stadtman, 1952) has shown that the major source of carbon dioxide is from the carboxyl group of amino acid via Strecker type degradation. Carbon dioxide is also formed during oxidation of amino-acids by Fenton reagents ($H_2O_2+Fe^{++}$) (Stadtman, 1991). We also noted that EDTA, and ambient laboratory light in the presence of phosphates, influenced the formation of carbon dioxide, The hydroxyalkyl radicals formed may also undergo dehydration & decarboxylation reaction as suggested by Steenken (Steenken, 1973). Davies (Davies, 1996) has recently shown that $Fe_2$-EDTA alkoxy radical can give rise to C-terminal decarboxylation with the release of $CO_2$ radical. Vasquez-Vivar (Vasquez-Vivar, 1997) observed that keto-carboxylic acids might undergo both a one or two electron oxidative decarboxylation by Fe/EDTA and hydrogen peroxide respectively.

Fluorescence formation: Non-enzymatic glycation reaction gives rise to fluorescent products. In vivo, the extent of fluorescence formation in tissues with long half-life, such as collagen, is generally observed to be proportional to age except in diabetic patients. In diabetes, a disease characterized by hyperglycemia, the extent of collagen fluorescence is considerably higher than in age matched non-diabetic population reflecting the increased accumulation of advanced glycation end (AGE) products. In our study, fluorescence, formation was increased by phosphate, ribose, light, EDTA, and interaction between phosphate-light. The effect of phosphate on NEG and fluorescence formation is described in detail below. Oxygen decreased fluorescence probably by quenching. The interaction of phosphate and light suggests the participation of radicals.

Consumption of CSZ-Lysine and formation of P1, P2, & P3: Consumption of CBZ-lysine was associated with phosphate, oxygen, and ribose (Table III) and with acidity, fluorescence, and P2 formation (Table V). From this, one may infer that CBZ-lysine may be used up in more than one pathway with glycoxidation being the predominant one generating acidity and fluorescence with P2 may be a product of this reaction.

Effect of phosphate: Phosphate, as an inorganic buffer salt or as a phosphate-ester of reducing sugar, accelerates Maillard reaction by facilitating enolization. Other anionic buffers such as arsenate and carbonate also catalyze this reaction (Spoehr 1934). These anions catalyze the formation of 1-2 enediol tautomer and stabilize it by forming adducts. Amino acids, cyanides (Robertson, 1981), osmium tetraoxide, and phenolate ions are also known to form adducts with enediols.

The autoxidation of reducing sugars occurs rapidly under alkaline conditions (DeWit, 1979). Hough (Hough, 1967) and Thornalley et al. (Thornalley, 1984} observed the rate of autoxidation of monosaccharides to be in the order of phosphates>HEPES>Tris under physiological conditions. They attributed this to the ability of the monosaccharides to form enediol in the same order. Wolff and Hunt (Wolff, 1991; Wolff 1989) in their investigation of glucose autoxidation and protein modification, observed that increasing concentration of phosphate produced a proportionally increased amount of ketoaldehyde as well as glycation of protein. Watkins et al., (Watkins, 1987) observed that the kinetics of glycation of RNAase, lysozome, cytochrome, and hemoglobin were substantially faster in phosphate as compared to cationic buffers. Based on kinetic investigation of glycation they concluded that phosphates facilitate the Amadori rearrangement. Basic proteins like RNAase, lysozome, and cytochrome c, were glycated more than acidic proteins like albumin and Mb.

Borsook and Wastcnenys (Borsook, 1925) and Schwimmer (Schwimmer, 1953) observed that phosphated sugars such as, glucose 6-phosphate and fructose 6-phosphate browned more rapidly than glucose and fructose. They further noticed that phosphate buffer salt considerably accelerated this browning process. Kato (Kato, 1956) and Webb (Webb, 1935) reported that phosphates enhance the overall rate of browning or fluorescence. Burton et al; (Burton, 1963) also observed similar enhancement of glucose glycine reaction by phosphate; the presence of trace amounts of iron also accelerated the Maillard reaction.

In spite of numerous examples of the enhancement of various stages of Maillard reaction by phosphates, its catalytic effect has been undermined as transition metals also exhibit similar effect (Burton, 1963) (Markuze, 1963). Micromolar amounts of iron, the levels usually present in most buffer solutions, are enough to induce autoxidation physiological pH (Buettner, 1988). In all the above cases there is no clear experimental evidence that care was taken to thoroughly remove trace metals from reagents nor was the amount of trace metals in such reagents determined.

In face of this controversy, our data suggests that phosphates may significantly and independently influence the Maillard reaction. In our experiment, the greatest source of trace metals, on a molar basis, was CBZ-lysine present in all the experiments. Thus, the effect of buffers was obtained against approximately the same amount of trace metals. Other supportive evidence that phosphates play an important role are as follows. Iron is not soluble in water at pH 7.4. They may exist at that pH as a mixed aquo-chelated complex at physiological pH. The redox potential of the Fe(III)/Fe(II) is high and is significantly changed by ligands (see Table V). Wang (Wang, 1978), de Figueiredo (de Figueiredo 1981), and Bobbio (Bobbio, 1973) observed that copper accelerated browning of glucose-glycine in a buffer-free system considerably decreased from 500% at pH 3 to 21% at pH 6.2, however, in presence of phosphates at 6.5 the reaction was considerably enhanced (Markuze, 1963). Phosphates are also known to catalyze the oxidation of ferrous ion by oxygen (Kurimura, 1969; Tadolini, 1987; Biaglow, 1997) as well as the reduction of ferric ions by reducing agents (Goto, 1970; Mitra, 1985) at neutral pH. Reinke (Reinke, 1994) have postulated the primary oxidant formed during $Fe^{2+}$ autoxidation in phosphate to be an iron-oxygen-phosphate complex such as a ferryl species. Similarly, fenyl-$O_2$-EDTA complex have been proposed as intermediate in the reaction of Fe/EDTA reaction with $H_2O_2$ (Rush, 1986). Taborsky (Taborsky, 1972) observed that phosphate ions strongly influenced the reaction between ferrous ions and cytochrome c. Fransson (Fransson, 1996) observed that phosphates, free of metal contaminants, influenced the oxidation of methionine in the presence of oxygen via formation of phosphorylated sulfonium ion formation. They also observed a significant interaction between phosphate and visible light and suggested the participation of free radicals. Reinke (Reinke, 1995) observed that inorganic phosphates markedly influenced the rates of free radical formation in liver microsomes. Thus, in biological medium, the ligand gives the trace metal its catalytical properties.

Effect of Tris and Good's buffer: Tris had minimum effect on pH or production of carbon dioxide, Interestingly, it also decreased fluorescence probably by quenching hydroxy radical. Shiraishi et al. (Shiraishi, 1993) observed that interactions of hydroxyl radicals with Tris and Good's buffer may produce formaldehyde. Adhikari and Tappell (Adhikari, 1973) have reported that polyvalent cation complex with melanoidins, resulting in diminished florescence; and perhaps Tris behaves similarly. Hopes and Tris are also known to form secondary radicals by effectively scavenging oxygen radicals from the iron catalyzed Huber-Weiss process and hydrogen peroxide (Murphy, 1974; Halliwell, 1986; Grady, 1998; Saprin, 1998; Burkitt, 1991).

Effect of Light: Bohart (Bohart, 1995) observed that light had a pronounced effect on Maillard products under certain conditions. When samples of a solution of D-glucose-glycine were sealed under nitrogen, those stored at 50° C. in laboratory illumination became darker than those kept in dark. However, when partially browned solutions under air or oxygen were exposed to light their color gradually bleached. Mizutari et al. (Mizutari, 1997) observed higher levels of CML in sun-exposed areas than sun-unexposed areas of the skin.

Effect of EDTA on responses: Transition metals, characterized by their incomplete d-orbitals, have the ability to rearrange their electronic configuration. For example, in Fe(II) one such rearranged state is the intermediate spin (S=1) with two unpaired electrons. Once this reorganization has occurred coupling between the unpaired electrons on both dioxygen ground state ($^3\Sigma_g^-$) and iron takes place resulting in the formation of iron dioxygen bond (McClure, 1960). The reaction between dioxygen and Fe(II) may also occur with electronic reorganization within the dioxygen singlet states. In biological medium oxygen is reduced to water through a four electron reduction process with the concomitant consumption of two equivalents of protons. Trace metals may easily donate the electrons during this process and thus influence the out come of this reaction. This step completes the oxidation cycle. In presence of reducing agents, the trace metal is reduced to its initial oxidation state and the cycle is completed with trace metals acting as a catalyst. The above 2±7 set of reactions is shown in scheme IV. The rate at which trace metal ions accept or donate their electrons is governed by redox potentials, concentration of ions and substrates, and the size of the ligand with smaller ligands favoring faster reaction rates. The redox potential for a given metal ion is strongly influenced by the type of ligand, their orientation, and electron-delocalization onto the ligand. Examples of some one-electron redox couples of Fe(II)/Fe(III) and its complexes including EDTA is given in Table VI, For iron to catalyze the formation of oxygen reactive species in biological medium requires the availability of at least one coordination site that is open or occupied by a readily dissociable ligand such as water (Graf, 1984). The site also needs to be free of steric hindrance so that either oxygen species or a reducing sugar can be accommodated in the complex to facilitate the transfer of electrons. As most chelators decrease the redox potential and thereby facilitate the electron transfer process, their inhibitory characteristics usually stem from their steric features. Wolff and Dean (Wolff, 1987) in their study of glucose autoxidation observed that trace metal chelators exhibited a peculiar biphasic response in which increasing concentration of chelators showed decreasing inhibitory effect on attachment of glucose to BSA. They attributed this behavior as evidence for two different pathways for glucose attachment, one dependent on trace metals and the other independent of metal. We believe that the later pathway represents the general acid-base catalytic effect of polyanion buffers.

The importance of amino acids, polyanions, and transition metals is their ability to catalyze the enolization reaction at physiological pH (Shallenberger, 1984) and facilitate the transfer of electron from the radical anion to oxygen. In nitrogen nucleophilic reactions, the carbonyl carbon of open-chain form of sugar reacts with an amino group to form a carbinol-amine intermediate. In presence of excess reactants, the carbinol-amine intermediate can dehydrate to form a Schiff base. If the reducing sugar is an aldose, the Schiff base under acidic conditions rearranges to 1,2-eneaminol through a sigmatropic shift, which later ketonizes to an Amadori product. Reversible reactions generate the carbinol-amine, Schiff base (Hayashi, 1986) (Namiki, 1975) and the Amadori products (Hodge, 1953). The Amadori product, a ketoamine (Yaylayan, 1994), through a series of substitution, rearrangement, and dehydration steps, give rise to highly reactive dicarbonyl sugar compounds that culminate in forming the final (AGE) products. Pentosidine and pyralanes are some of the products found in-vivo and used as biomarkers for the NEG reaction. The original NEG mechanism did not emphasize oxidation or free radical involvement but focused more on the formation of Amadori products that altered surface charge, hydrogen bonding capability, cellular recognition, and formed complex products capable of cross-linking (Pongor, 1984; Brownlee, 1994; Harding, 1985).

EXAMPLE 2

This example illustrates the relationship of serum phosphate levels, serum glucose levels and glycation as indicated by HbA1c levels in humans.

We performed a retrospective chart review of blood data of our veterans at the Veterans Medical Center stored in the computer database. The samples were restricted to morning (before 8:00 am) blood draw data that included HbA1c, serum phosphate, glucose, over a four-month period. Only patients with normal inorganic phosphate levels (2.0-5.0 mg/dl) were used for the study and our results are shown as a three-dimensional plot in FIG. 5. The x-axis and y-axis represents average phosphate and glucose level over a four-month period and the z-axis represents the HbA1c values. As one would expect the extent of HbA1c level increases with increasing average serum glucose. However, it is interesting to note that for any given value of glucose, the value of HbA1c increases with increasing levels of serum phosphate. This is a non-linear effect with the interaction more pronounced at lower concentrations of glucose and phosphate than at higher. Thus, the trend observed in vitro is also observed in vivo that is, HbA1c is modulated by factors other than reducing sugars and phosphate is one such factor.

Figure 5:
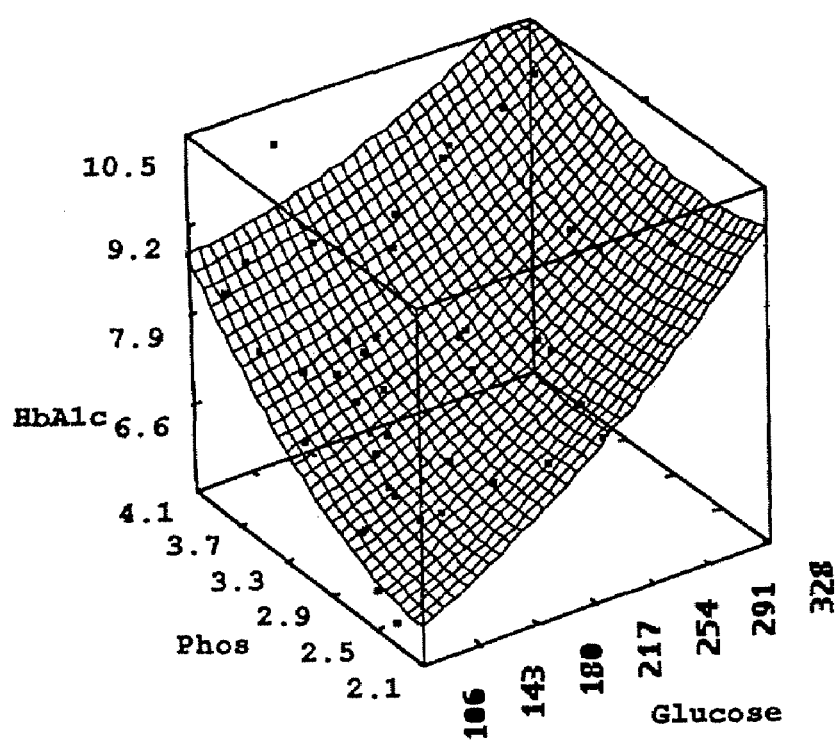
FIG. 5 illustrates a three-dimensional plot of values obtained from patients in which the x-axis and y-axis represent average phosphate and glucose level over a four-month period and the z-axis represents the HbA1c values.

The relationship of serum phosphate, serum glucose and serum HbA1c values is represented by the plane illustrated in FIG. 5. This plane is defined by the equation $$G = A \times Hb - B \times P_i C$$

in which G is serum glucose concentration, Hb is measured serum HbA1c concentration, $P_i$ is measured serum inorganic phosphate concentration, A is about 76, B is about 67 and C is about 212. This equation can be used to obtain an estimated value for glucose levels based upon phosphate and HbA1c levels as follows.

$$G_e = A \times Hb - B \times P_i C$$

in which $G_e$ is estimated serum glucose concentration and Hb, $P_i$, A, B and C are as defined above. This estimated value for glucose can then be compared with the measured values of glucose and both can be compared to reference values for glucose.

All references cited in this specification are hereby incorporated by reference. Any discussion of references cited herein is intended merely to summarize the assertions made by their authors and no admission is made that any reference or portion thereof constitutes relevant prior art. Applicants reserve the right to challenge the accuracy and pertinency of the cited references.

REFERENCES

1. V. M. Monnier, M. Glomb, A. Eigawish, D R. Sell, *Diabetes* 45 *Suppl* 3, S67 (1996).
2. B. J. Ortwerth, S M. Slight, M. Prabhakaram, Y. Sun, J. B. Smith, *Biochimica et Biophysica Acta* 1117, 207 (1992).
3. A. Papoulis, Y. al-Abed, R. Bucala, *Biochemistry* 34,648 (1995).
4. A. T. Lee, A. Cerami, *Progress in Clinical & Biological Research* 304, 291 (1989).
5. R. Ikan, *The Maillard Reaction Consequences for the chemical and life sciences*, R. Ikan, Ed. (John Wiley & Sons, New York, 1996), p. 161.
6. V. M. Monnier, *Journal of Gerontology* 45, B 105 (1990).
7. V. M. Monnier, *Progress in Clinical & Biological Research* 304, 1 (1989).
8. V. M. Monnier, A. Cerami, *Science* 211, 491 (1981).
9. P. J. Thornalley, *Environmental Health Perspectives* 64, 297 (1985).
10. S. P. Wolff, Z. A. Bascal, J. V, Hunt, *Progress in Clinical & Biological Research* 304, 259 (1989).
11. M. Namiki, 1. Hayashi, *J. Agric. Food Chem.* 23, 487 (1975).
12. T. H~ayashi, M. Namiki, *Amino-carbonyl reactions in infood and biological systems*, E. Fujimori, M. Namiki and H. Kato, Eds. (Elsevier, Amsterdam, 1986), p. 29.
13. I. Sakari, K. Sugioka, M. Nakano, *Biochim. Biophysics. Acta* 1043, 27 (1990).
14. K. J. Wells-Knecht, D V. Zyzak, J. E. Litchfield, S. R. Thorpe, J. W. Baynes, *Biochemistry* 34, 3702 (1995).
15. T. Miyata, et al, Nephrology, Dialysis, Transplantation 11 Suppl 5, 27 (1996).
16. V. M. Monnier, et al, Nephrology, Dialysis, Transplantation 11 Suppl 5, 20 (1996).
17. T. Miyata, K. Maeda, K. Kurokawa, C. van Ypersele de Strihou, Nephrology, Dialysis, Transplantation 12, 255 (1997).
18. C. A. Colaco, M. D. Ledesma, C R. Harrington, J. Avila, Nephrology, Dialysis, Transplantation 11 Suppl 5, 7 (1996).
19. J. Thome, et al, Nervenar: t 67, 924 (1996).
20. T. Kimura, et al, Neuroreport 6, 866 (1995).
21. M A. Smith, et al, Annals of the New York Academy of Sciences 738, 447 (1994).
22. T. Kimura, et al, Néuroscience Letters 219, 95 (1996).
23. G. E. P. Box, W. G. Hunter, J. S. Hunter, Statistics for Experimenters An introduction to design, data analysis, and model building (John Wiley & Sons, Inc.; New York, 1978).
24. S. J. Cortes, T. L. Mega, R. L. van Etten, J. Org. Chem. 56, 943 (1991).
25. P. R. Smith, P. J. Thornalley, Biochemistry International 28, 429 (1992).
26. F. M. Stadtman, C O. Chichester, Mackinney O., Journal of the American Chemical Society 74, 3194 (1952).
27. A. Katchaisky, N. Sharon, Biochim. Biophysics. Acta 10, 290 (1953).
28. M. U. Ahmed, S. R. Thorpe, J. W. Baynes, Journal of Biological Chemistry 261, 4889 (1986).
29. B. B. Benson, D. Krause, J. Chem. Phys. 64, 689 (1982).
30. H. A. Spoehr, H. W. Mimer, J. Am. Chem. Soc 56, 2068 (1934).
31. M. Clinton, R. S. Hubbard, Journal of Biological Chemistry 119, 467 (1937).
32. E. R. Stadtman, B. S. Berlett, J. Biol. Chem. 266, 17201 (1991).
33. S. Steenken, Schultze-Frohlidine, Tetrahedron Lett. 653 (1973).
34. 34, M. J. Davies, Archives of Biochemistry & Biophysics 336, 163 (1996).
35. J. Vasquez-Vivar, A. Denicola, R. Radi, O. Augusto, Chemical Research in *Toxicology* 10 (7), 786 (1997).
36. P. Robertson, S. E. Fridovich, H. P. Misra, 1. Fridovich, *Archives of Biochemistry & Biophysics* 207-2, 282 (1981).
37. L. Bough, A. C. Richardson, 1967), p. 274.
38. P. Thornalley, S. Wolff, J. Crabbe, A. Stem, *Biochimica et Biophysica Acta* 797, 276 (1984).
39. J. V. Hunt, S. P. Wolff, *Free Radical Research Communications* 12-13 Pt 1, 115 (1991).
40. N. O. Watkins, C I. Neglia-Fisher, D. O. Dyer, S. R. Thorpe, J. W. Baynes, *Journal of Biological Chemistry* 262, 7207 (1987).
41. H. Borsook, H. Wasteneys, *Biochemistry Journal* 19, 1128 (1925).
42. S. Schwimmer, H. S. Olcott, *Journal of the American Chemical Society* 75, 4855 (1953).
43. H. Kato, *Bull. Agr. Chem. Soc. Japan* 20 supp 1, 273 (1956).
44. B. H. Webb, *J. Dairy Science* 2, 81 (1935).
45. H. S. Burton, D. J. McWeeney, D. 0. Biltcliffe, *J. Food Sci.* 28, 631 (1963).
46. Z. Markuze, *Roczniki Panstwowego Zakladu Hig.* 14, 65 (1963).
47. G. R. Buettner, *J. Biochem. Biophys. Methods* 16, 27 (1988).

48. S M. Wang, P A. Bobbio, F. O. Bobblo, *An. Acad. Bras. Cienc.* 50, 55 (1978).
49. F. O. Bobbio, P. A. Bobbio, L. M. V. Trevisan, *Lebensm. Wiss. Technol.* 6, 215 (1973).
50. Y. Kurimura, *Bull. Chem. Soc. Jpn.* 42 (8), 2238 (1969).
51. B. Tadolini, A. M. Sechi, *Free Radical Res. Commun.* 4 (3), 161 (1987).
52. J. E. Biaglow, Kachur, A. V., *Radiation Res* 142 (2), 181 (1997).
53. K. Goto, H. Tamura, M. Nagayama, *Inorganic Chemistry* 9, 963 (1970).
54. Mitra A. K., M L. Matthews, *International Journal of Pharmaceutics* 23, 185 (1985).
55. L. A. Reinke, J. M. Rau, P B. McCay, *Free Radical Biology & Medicine* 16 (4), 485 (1994).
56. J. D. Rush, W. H. Koppenol, *J. Biol. Chem.* 261 (15), 6730 (1986).
57. O. Taborsky, *Biochemistry* 11 (5), 729 (1972).
58. L. A. Reinke, D R. Moore, J. R. M. P. B. Rau., *Archives of Biochemistry & Biophysics* 316, 758 (1995).
59. H. Shiraishi, M. kataoka, Y. Morita, J. Umemoto, *Free Radical Res. Commun.* 19 (5), 315 (1993).
60. H. R. Adhikari, A L. Tappel, *J Food Sci.* 38, 486 (1973).
61. P. A. Murphy, J. S, Lin, H. S. Olcott, *Archives of Biochemistry & Biophysics* 164, 776 (1974).
62. B. Halliwell, J. M. Gutteridge, *Archives of Biochemistry & Biophysics* 246, 501 (1986).
63. A M. Saprin, L. H. Piette, *Archives of Biochemistry & Biophysics* 180, 480 (1998).
64. M. J. Burkitt, B. C. Gilbert, *Free Radical Res. Commun.* 14, 107 (1991).
65. K. Mizutari, T. Ono, K. Ikeda, K. Kayashima, S. Horiuchi, *Journal of Investigative Dermatology* 108, 797 (1997).
66. D. S. McClure, *Radiation Res. suppl* 2, 218 (1960).
67. E. Graf, J. R. Mahoney, R. G. Bryant, J. W. Eaton, *J. Biol. Chem.* 259 (6), 3620 (1984).
68. S. P. Wolff, R. I. Dean, *Biochemical Journal* 245, 243 (1987).
69. R. S. Shallenberger, *Food Chem.* 15, 1 (1984).
70. J. E. Hodge, *J. Agric. Food Chem.* 1, 928 (1953).
71. V. A. Yaylayan, A. Huyghues-Despointes, *Critical Reviews in Food Science & Nutrition* 34, 321 (1994).
72. S. Pongor, P. C. Ulrich, F. A. Bencsath, A. Cerami, Proceedings of the National Academy of Sciences of the United States of America 81, 2684 (1984).
73. M. Brownlee, *Diabetes* 43, 836 (1994).
74. J. J. Harding, *Adv. Prot. Chem.* 37, 247 (1985).
75. K. Kunika, M. Itakura, K. Yamashita, *Life Sciences* 45, 623 (1989).
76. K. Kunika, M. Itakura, K. Yamashita, *Diabetes Research and Clinical Practice* 13, 37 (1991).
77. K. Kunika, K. Yamashita, M. Itakura, *Diabetes Research and Clinical Practice* 17, 9 (1992).
78. D R. Sell, V. M. Monnier, *J. Clin. Invest* 85, 380 (1990).
79. D R. Sell, et al, *Diabetes Metabolism Reviews* 7, 239 (1991).
80. P. Odetti, J. Fogarty, D R. Sell, V. M. Monnier, *Diabetes* 41, 153 (1992).
81. J. Sabater, et al, *Am. J. Nephrol.* 11, 370991).
82. R. J. Haley, D. M. Ward, Am. *J. Kidney Dis.* 8, (2), 115 (1986).
83. Anonymous, *Alzheimer Disease* (1994).
84. M. P. Vitek, et al., *Proceedings of the National Academy of Sciences of the United States of America* 91 (11), 4766 (1994).
85. A. Takedo, et al., Neuroscience Letters 221 (1), 17 (1996).
86. G. Lee, N. Cowan, M. Kirschner, Science 239, 285 (1988).
87. S. C. Seldon, T. D. Pollard, J. Biol Chem 258, 7064 (1983).
88. M. Butler, M L. Shelanski, *J Neurochem* 47, 1517 (1986).
89. V. M. Lee, B. J. Balm, L. Otvos, Q. Irojanowski, *Science* 251, 675 (1991).
90. M. Abdel-Ghany, A. K. El-Sebae, D. Shalloway, *J. Biol Chem* 268 (16), 11976 (1993).
91. S. S. Krishnan, D. R. McLachlan, B. Krishnan, S. S. Fenton, J. E. Harrison, *Sci. Total Environ.* 71 (1), 59 (1988).
92. H. Yoshida, F. Yoshimasu, *Nippon Rinsho* 54 (1), 111 (1996).
93. Nishida Y, Ito 5, *Z. Naturforsch* 50 (7-8), 571 (1995).
94. W. R. Mundy, T M. Freudenrich, P. R. Kodavanti, *Mol. Chem. Neuropathol.* 32 (1-3), 41 (1997).
95. S. Toda, Y. Yase, *BioL Trace Elem. Res.* 61 (2), 207 (1998).
96. T. Iarkka, N. Yli-Mayiy, R. M. Mannermaa, K. O. J. Majamaa, *Biochim. Biophysics. Acta* 1180 (3), 294 (1993).
97. M. D. Ledesma, Bonay, P, C. A. Colaco, J. Avila, *J. Biol Chem* 269 (34), 21614 (1994).
98. S. D. Yan, et al., *Nat. Med* 1 (7), 693 (1995).

The present application includes the following aspects:

1. A method of monitoring glycemia status in a diabetic patient, the method comprising:

(a) measuring in a diabetic patient, serum concentrations of HbA1c, glucose and inorganic phosphate and (b) comparing measured concentrations of HbA1c, glucose, and inorganic phosphate with reference concentrations of HbA1c, glucose, and inorganic phosphate, wherein if any one or more of measured concentrations of HbA1c, glucose, and inorganic phosphate exceed reference concentrations, glycemia is deemed to not be controlled.

2. A method according to Aspect 1, wherein reference concentration for serum glucose is about 140 mg/dL, reference concentration for serum inorganic phosphate is about 4.5 mg/dL and reference concentration for serum HbA1c is about 7%.

3. A method according to Aspect 2, wherein (i) if the measured serum glucose concentration exceeds about 140 mg/dL, serum glucose concentration is deemed to not be controlled; (ii) if the measured serum inorganic phosphate concentration exceeds 4.5 mg/dL, serum inorganic phosphate concentration is deemed to not be controlled; and (iii) if the measured serum HbA1c concentration exceeds 7% (w/v), both serum glucose concentration and serum inorganic phosphate concentrations are deemed to not be controlled.

4. A method according to Aspect 3 further comprising managing glycemia level in the patient, wherein said managing comprising administering one or more agents that decrease serum glucose concentration, administering one or more agents that decrease serum inorganic phosphate concentration or administering one or more agents that decrease serum glucose concentration and one or more agents that decrease serum inorganic phosphate concentration.

5. A method according to Aspect 4, wherein (i) if measured serum glucose concentration exceeds about 140 mg/dL, glycemia is deemed to not be controlled and managing comprises administering one or more agents that decrease glucose concentration; (ii) if measured serum inorganic phosphate concentration exceeds about 4.5 mg/dL, inorganic phosphate concentration is deemed to not be controlled and managing comprises administering one or more agents that decrease inorganic phosphate concentration; and (iii) if measured serum HbA1c concentration exceeds 7% (w/v), both glucose concentration and inorganic phosphate concentration are deemed to not be controlled and managing comprises administering one or more agents that decrease glucose concentration and one or more agents that decrease inorganic phosphate concentration.

6. A method of Aspect 5, wherein the one or more agents that decrease serum phosphate concentration are selected from the group consisting of a diuretic having carbonic anhydrase activity, a phosphate binder and a combination thereof.

7. A method of Aspect 6, wherein the diuretic is acetazolamide, dichlorphenamide, methazolamide, furosemide or a combination thereof.

8. A method of Aspect 6, wherein the phosphate binder is aluminum hydroxide, calcium hydroxide, a calcium salt, magnesium hydroxide, a magnesium salt, lanthanum carbonate, a phosphate binding cationic polymer or a combination thereof.

9. A method of Aspect 8, wherein the calcium salt is calcium acetate, calcium carbonate, calcium gluconate or a combination thereof.

10. A method of Aspect 8, wherein the magnesium salt is magnesium acetate, magnesium carbonate, magnesium gluconate or a combination thereof.

11. A method of Aspect 8, wherein the phosphate binder is lanthanum carbonate.

12. A method of Aspect 8, wherein the phosphate binding cationic polymer is sevelamer hydrochloride.

13. A method of Aspect 5, wherein the one or more agents that decrease serum glucose concentration are insulin, a sulfonylurea, a biguanide compound, a meglitinide compound, a compound that acts upon starch digestion or metabolism or a combination thereof.

14. A method of monitoring glycemia status in a diabetic patient, the method comprising:

(a) measuring in a diabetic patient, serum concentrations of HbA1c, inorganic phosphate and glucose;

(b) calculating estimated glucose concentrations based upon equation:

$$G_e = A \times Hb - B \times P_i - C$$

wherein $G_e$ is estimated serum glucose concentration, Hb is measured serum HbA1c concentration, $P_i$ is measured serum inorganic phosphate concentration, A is about 76, B is about 67 and C is about 212; and (c) comparing measured serum glucose concentration and estimated serum glucose concentration to a reference glucose concentration, wherein if either or both of the measured serum glucose concentration and the estimated serum glucose concentration exceed the reference glucose concentration, glycemia is deemed to not be controlled.

15. A method of Aspect 14, wherein the reference serum glucose concentration is about 140 mg/dL.

16. A method of Aspect 15, further comprising managing glycemia level in the patient, wherein said managing comprising administering one or more agents that decrease serum glucose concentration, administering one or more agents that decrease serum inorganic phosphate concentration or administering one or more agents that decrease serum glucose concentration and one or more agents that decrease serum inorganic phosphate concentration.

17. A method according to Aspect 16, wherein (i) if measured serum glucose concentration exceeds about 140 mg/dL and estimated serum glucose concentration does not, glycemia is deemed to not be controlled and managing comprises administering one or more agents that decrease serum glucose concentration; (ii) if estimated serum glucose concentration exceeds about 140 mg/dL and measured serum glucose concentration does not, inorganic phosphate concentration is deemed to not controlled and managing comprises administering one or more agents that decrease serum inorganic phosphate concentration and (iii) if both measured serum glucose concentration and estimated serum glucose concentration exceed about 140 mg/dL, glycemia and inorganic phosphate concentrations are deemed to not be controlled and managing comprises administering one or more agents that decrease serum glucose concentration and one or more agents that decrease serum inorganic phosphate concentration.

18. A method of Aspect 17, wherein the one or more agents that decreases serum inorganic phosphate concentration are selected from the group consisting of a diuretic having carbonic anhydrase activity, a phosphate binder and a combination thereof.

19. A method of Aspect 18, wherein the diuretic is acetazolamide, dichlorphenamide, methazolamide, furosemide or a combination thereof.

20. A method of Aspect 18, wherein the phosphate binder is aluminum hydroxide, calcium hydroxide, a calcium salt, magnesium hydroxide, a magnesium salt, lanthanum carbonate, a phosphate binding cationic polymer or a combination thereof.

21. A method of Aspect 20, wherein the calcium salt calcium acetate, calcium carbonate, calcium gluconate or a combination thereof.

22. A method of Aspect 20, wherein the magnesium salt is magnesium acetate, magnesium carbonate, magnesium gluconate or a combination thereof.

23. A method of Aspect 20, wherein the phosphate binder is lanthanum carbonate.

24. A method of Aspect 20, wherein the phosphate binding cationic polymer is sevelamer hydrochloride.

25. A method of Aspect 17, wherein the one or more agents that decrease serum glucose concentration are insulin, a sulfonylurea, a biguanide compound, a meglitinide compound, a compound that acts upon starch digestion or metabolism or a combination thereof.

26. An assay kit for determining glycemia status in a patient, the kit comprising one or more reagents for measuring serum glucose levels, one or more reagents for measuring HbA1c levels and one or more reagents for measuring serum inorganic phosphate levels in a sample from the patient.

27. An assay kit of Aspect 26, wherein the one or more reagents for measuring serum glucose levels comprise glucose oxidase or hexokinase.

28. An assay kit of Aspect 26, wherein the one or more reagents for measuring serum HbA1c levels comprise a fructosyl amino acid oxidase.

29. An assay kit of Aspect 28, wherein the fructosyl amino acid oxidase comprises fructosyl valine oxidase.

30. An assay kit of Aspect 26, wherein the one or more reagents for measuring serum inorganic phosphate levels comprises ammonium molybdate.

31. An assay kit of Aspect 26, wherein the one or more reagents for measuring serum glucose levels comprise glucose oxidase or hexokinase; the one or more reagents for measuring serum HbA1c levels comprises fructosyl valine oxidase; and the one or more reagents for measuring serum inorganic phosphate levels comprises ammonium molybdate.

What is claimed is:

1. A method of managing glycation risk in a diabetic patient, the method comprising:
    (a) measuring in a diabetic patient, serum concentrations of HbA1c, inorganic phosphate, and glucose; and
    (b) providing a treatment selected on the basis of the measured serum HbA1c concentration, the serum inorganic phosphate concentration and the serum glucose concentration,
wherein if the serum HbA1c concentration exceeds 7% and at least one of (i) the serum glucose concentration exceeds about 140 mg/dL and (ii) the measured serum inorganic phosphate concentration exceeds 4.5 mg/dL, the treatment comprises administering one or more agents that decrease serum inorganic phosphate concentration.

2. A method according to claim 1, further comprising determining in the diabetic patient serum inorganic phosphate concentration, wherein if the serum HbA1c concentration exceeds 7% and at least one of (i) the serum glucose concentration exceeds about 140 mg/dL and (ii) the measured serum inorganic phosphate concentration exceeds 4.5 mg/dL, the treatment comprises administering one or more agents that decrease serum inorganic phosphate concentration.

3. A method of claim 1, wherein the one or more agents that decrease serum inorganic phosphate concentration are selected from the group consisting of a diuretic having carbonic anhydrase inhibitor activity, a phosphate binder and a combination thereof.

4. A method of claim 3, wherein the diuretic is acetazolamide, dichlorphenamide, methazolamide, furosemide or a combination thereof.

5. A method of claim 3, wherein the phosphate binder is aluminum hydroxide, calcium hydroxide, a calcium salt, magnesium hydroxide, a magnesium salt, lanthanum carbonate, a phosphate binding cationic polymer or a combination thereof.

6. A method of claim 5, wherein the calcium salt is calcium acetate, calcium carbonate, calcium gluconate or a combination thereof.

7. A method of claim 5, wherein the magnesium salt is magnesium acetate, magnesium carbonate, magnesium gluconate or a combination thereof.

8. A method of claim 5, wherein the phosphate binder is lanthanum carbonate.

9. A method of claim 5, wherein the phosphate binding cationic polymer is sevelamer hydrochloride.

10. A method of claim 1, wherein the one or more agents that decrease serum glucose concentration are insulin, a sulfonylurea, a biguanide compound, a meglitinide compound, a compound that acts upon starch digestion or metabolism or a combination thereof.

11. A method of managing glycation risk in a diabetic patient, the method comprising:
    (a) measuring in a diabetic patient, serum concentrations of HbA1c and glucose;
    (b) calculating serum inorganic phosphate concentration based upon equation:

$$Pi=(A \times Hb-G-G)/B$$

wherein G is serum glucose concentration, Hb is measured serum HbA1c concentration, $P_i$ is serum inorganic phosphate concentration, A is about 76, B is about 67 and C is about 212; and
    (c) providing a treatment selected on the basis of the serum HbA1c concentration, the serum glucose concentration and the serum Pi concentration, wherein if the serum HbA1c concentration exceeds 7% and at least one of i) the serum inorganic phosphate concentration exceeds 4.5 mg/dL and ii) the serum glucose concentration exceeds about 140 mg/dL, the treatment comprises administering one or more agents that decrease serum inorganic phosphate concentration.

12. A method of managing glycation risk in a diabetic patient having a serum HbA1c concentration of at least 7%, the method comprising:
    (a) determining in the diabetic patient serum glucose concentration and serum inorganic phosphate concentration; and
    (b) providing a treatment, wherein if the glucose concentration does not exceed about 140 mg/dL and the serum inorganic phosphate concentration exceeds 4.5 mg/dL, the treatment comprises administering to the patient one or more agents that decrease serum inorganic phosphate concentration, and wherein if the glucose concentration exceeds about 140 mg/dL and the serum inorganic phosphate concentration exceeds 4.5 mg/dL, the treatment comprises administering to the patient one or more agents that decrease serum inorganic phosphate concentration and one or more agents that decrease serum glucose concentration.

13. A method in accordance with claim 12, further comprising determining in the diabetic patient serum inorganic phosphate concentration, wherein if at least one of i) the serum inorganic phosphate concentration exceeds 4.5 mg/dL and ii) the serum glucose concentration exceeds about 140 mg/dL, the treatment comprises administering one or more agents that decrease serum inorganic phosphate concentration.

14. A method in accordance with claim 12, wherein the determining serum glucose concentration comprises measuring serum glucose concentration in a sample from the patient.

15. A method in accordance with claim 12, wherein the determining serum inorganic phosphate concentration comprises measuring serum inorganic phosphate concentration in a sample from the patient.

16. A method in accordance with claim 12, wherein the determining the serum glucose concentration comprises measuring the serum HbA1c concentration and the serum inorganic phosphate concentration, and calculating the serum glucose concentration in accordance with the relationship $G=A \times Hb-B \times Pi-C$, wherein Hb is serum HbA1c concentration (% wt/vol), G is serum glucose concentration (mg/dL), $P_i$ is serum inorganic phosphate concentration (mg/dL), A is about 76, B is about 67 and C is about 212.

17. A method in accordance with claim 12, wherein the determining serum inorganic phosphate concentration comprises measuring serum glucose concentration and serum Hb1Ac concentration, and calculating the serum inorganic phosphate concentration in accordance with the relationship $Pi=(A \times Hb-G-C)/B$, wherein Hb is serum HbA1c concentration (% wt/vol), G is serum glucose concentration (mg/dL), $P_i$ is serum inorganic phosphate concentration (mg/dL), A is about 76, B is about 67 and C is about 212.

* * * * *